United States Patent
Culic et al.

(10) Patent No.: US 7,989,600 B2
(45) Date of Patent: Aug. 2, 2011

(54) MACROLIDE COMPOUNDS CONTAINING BIOTIN AND PHOTO-AFFINITY GROUP FOR MACROLIDE TARGET IDENTIFICATION

(75) Inventors: Ognjen Culic, Zagreb (HR); Martina Bosnar, Zagreb (HR); Nikola Marjanovic, Zagreb (HR); Boris Mildner, Zagreb (HR); Linda Tomaskovic, Zagreb (HR); Sulejman Alihodzic, Zagreb (HR)

(73) Assignee: GlaxoSmithKline Istrazivacki Centar Zagreb D.O.O., Zagreb, Croatia ( * ) Notice: Subject to any disclaimer, the term of this patent is extended or adjusted under 35 U.S.C. 154(b) by 733 days.

(21) Appl. No.: 11/813,871

(22) PCT Filed: Jan. 13, 2006

(86) PCT No.: PCT/IB2006/001484
§ 371 (c)(1),
(2), (4) Date: Apr. 9, 2008

(87) PCT Pub. No.: WO2006/106440
PCT Pub. Date: Oct. 12, 2006

(65) Prior Publication Data
US 2008/0241959 A1    Oct. 2, 2008

Related U.S. Application Data

(60) Provisional application No. 60/644,333, filed on Jan. 14, 2005.

(51) Int. Cl.
*C07H 17/08* (2006.01)

(52) U.S. Cl. .................................................. 536/7.4

(58) Field of Classification Search .............. 536/7.4, 536/7.2
See application file for complete search history.

(56) References Cited

FOREIGN PATENT DOCUMENTS
JP    2005/095014    4/2005

OTHER PUBLICATIONS

Arevalo et al., "Synthesis and Biological Activity of Photoactive Derivatives of Erythromycin," *Journal of Medicinal Chemistry*, V32 N9, 1989, pp. 2200-2204.
Arevalo et al., *Journal of Biological Chemistry*, V263 N1, 1988, pp. 58-63.
Vince et al., *Antimicrobial Agents and Chemotherapy*, V9 N1, 1976, pp. 131-136.
Sherman et al., "Synthesis and biological investigation of new 4"-malonyl tethered derivatives of erythromycin and clarithromycin," *Bioorganic & Medicinal Chemistry Letters*, V 16 N6, 2006, pp. 1506-1509.
Fleming, "Chemical Reagents in Photoaffinity Labeling," *Tetrahedron*, V51 N46, 1995, pp. 12479-12520.

*Primary Examiner* — Elli Peselev
(74) *Attorney, Agent, or Firm* — Karen L. Prus

(57) ABSTRACT

The present invention relates to new macrolide compounds represented by the general structure I,

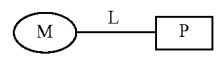

wherein M is a macrolide, P is a photo-affinity group bearing subunit containing biotin, and L is a linking molecule, and to their pharmaceutically acceptable salts and solvates, to processes and intermediates for their preparation and to the use of these compounds for the macrolide target identification.

6 Claims, 1 Drawing Sheet

Figure 1A
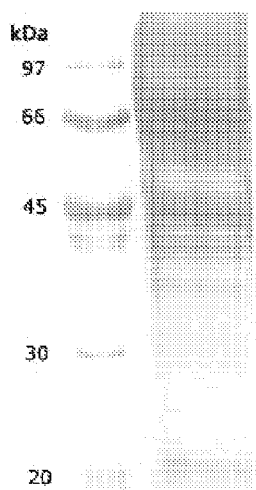
Figure 1B
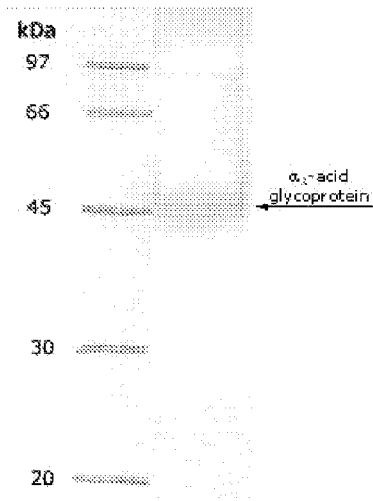
Figure 1

MACROLIDE COMPOUNDS CONTAINING BIOTIN AND PHOTO-AFFINITY GROUP FOR MACROLIDE TARGET IDENTIFICATION

This application is filed pursuant to 35 U.S.C. § 371 as a United States National Phase Application of International Application No. PCT/IB2006/001484filed Jan. 13, 2006, which claims priority from U.S. 60/644,333 filed Jan. 14, 2005.

This application claims priority to U.S. Provisional Application No. 60/644,333, filed Jan. 14, 2005, herein incorporated by reference.

FIELD OF THE INVENTION

The present invention relates to new macrolide compounds represented by the general structure I, to their pharmaceutically acceptable salts and solvates, to processes and intermediates for their preparation and to the use of these compounds for the macrolide target identification.

BACKGROUND OF THE INVENTION

Macrolide antibiotics accumulate preferentially within different cells of subjects, especially within phagocyte cells such as mononuclear peripheral blood cells, and peritoneal and alveolar macrophages. (Gladue, R. P. et al, *Antimicrob. Agents Chemother.* 1989, 33, 277-282; Olsen, K. M. et al, *Antimicrob. Agents Chemother.* 1996, 40, 2582-2585). Inflammatory effects of some macrolides have been described in the literature. For example, the anti-inflammatory effect of erythromycin derivatives (*J. Antimicrob. Chemother.* 1998, 41, 37-46; WO Patent Application No. 00/42055) and azithromycin derivatives has been described (EP Pat. Br. 0283055). Anti-inflammatory effects of some macrolides are also known from in vitro and in vivo studies in experimental animal models such as in zymosan-induced peritonitis in mice (*J. Antimicrob. Chemother.* 1992, 30, 339-348) and endotoxin-induced neutrophil accumulation in rat trachea (*J. Immunol.* 1997, 159, 3395-4005). The modulating effect of macrolides upon cytokines such as interleukin 8 (IL-8) (*Am. J. Respir. Crit. Care. Med.* 1997, 156, 266-271) and interleukin 5 (IL-5) (EP Pat. Br. 0775489 and EP Pat. Br. 771564) is known as well.

Macrolides have the property of accumulating within immune system cells recruited to the site of inflammation, especially phagocytic cells: Pascual A. et al. Clin. Microbiol. Infect. 2001, 7, 65-69. (Uptake and intracellular activity of ketolide HMR 3647 in human phagocytic and non-phagocytic cells); Hand W. L. et al. Int. J. Antimicrob. Agents, 2001, 18, 419-425. (Characteristics and mechanisms of azithromycin accumulation and efflux in human polymorphonuclear leukocytes); Amsden G. W. Int. J. Antimicrob. Agents, 2001, 18, 11-15. (Advanced-generation macrolides: tissue-directed antibiotics); Johnson J. D. et al. J. Lab. Clin. Med. 1980, 95, 429-439.(Antibiotic uptake by alveolar macrophages); Wildfeuer A. et al. Antimicrob. Agents Chemother. 1996, 40, 75-79. (Uptake of azithromycin by various cells and its intracellular activity under in vivo conditions); Scorneaux B. et al. Poult. Sci. 1998, 77, 1510-1521. (Intracellular accumulation, subcellular distribution, and efflux of tilmicosin in chicken phagocytes); Mtairag E. M. et al. J. Antimicrob. Chemother. 1994, 33, 523-536. (Investigation of dirithromycin and erythromycylamine uptake by human neutrophils in vitro); Anderson R. et al. J. Antimicrob. Chemother. 1988, 22, 923-933. (An in-vitro evaluation of the cellular uptake and intraphagocytic bioactivity of clarithromycin (A-56268, TE-031, a new macrolide antimicrobial agent); Tasaka Y. et al. Jpn. J. Antibiot. 1988, 41, 836-840. (Rokitamycin uptake by alveolar macrophages); Harf R. et al. J. Antimicrob. Chemother. 1988, 22, 135-140. (Spiramycin uptake by alveolar macrophages).

Macrolide antibiotics appear to have a promising role in the management of diseases of chronic airway inflammation, distinctly separate from their bactericidal activity. Over the last fifteen years, their success in human clinical trials, particular in diseases such as diffuse panbronchiolitis and cystic fibrosis, has prompted both in vitro and in vivo investigations to determine the mechanisms by which this family of antibiotics modulate the immune response. A large body of evidence suggests that macrolides directly target multiple components of the inflammatory cascade that occur independent of bactericidal/bacteriostatic effects. (W. C. Tsai, Current Pharmaceutical Design, 2004, 10, 3081-3093).

There is a great need to understand mechanisms that control inflammation within the lung. This imperative coincides with a revolution in cellular and molecular biology which should provide the tools necessary for lung biologists to clarifying the mechanism(s) by which macrolides exert immunomodulatory effects in the setting of pulmonary inflammation, and establishing potential therapeutic strategies based on the elucidated mechanism(s). For example, it was shown that azithromycin specifically binds to $\alpha_1$-acid glycoprotein from serum using dialysis in combination HPLC methods (Castearena et al., J Chemother. 1995, 7 Suppl 4:26-8).

Photoaffinity labeling is a technique in which a photochemically reactive molecular entity, specifically associated with a biomolecule, is photoexcited in order to covalently attach a label to the biomolecule, usually via intermediates (IUPAC Compendium of Chemical Terminology, 2nd Edition, 1997). Photoaffinity labeling is important methodology in biological science widely used for the analysis of structural aspects which are related to specific functions of the target biological macromolecular systems. The method requires photoreactive groups which generate highly reactive intermediates, usually nitrene and carbene as the key structure of photoaffinity probes (Hatanaka Y. et al., Heterocycles, 1993, 35, 997-1004).

The use of macrolide photoaffinity analogs allows the study of protein-macrolide interactions at the molecular level. Photoaffinity labeling technique can be used to determine which specific macrolide binding proteins are the targets of drugs.

BRIEF DESCRIPTIONS OF THE DRAWINGS

FIG. 1. Detection of $\alpha_1$-acid glycoprotein. FIG. 1A provides a silver stain. FIG. 1B provides a Western blot.

SUMMARY OF THE INVENTION

According to the known and established state of the art, compounds represented by Formula I, which are the object of the present invention, their pharmacologically acceptable salts and the method of their use for protein identification have hitherto not been described.

The present invention provides, by the use of a single reagent, macrolide conjugates with the ability to be photoaffinity cross-linked to other molecules, to be receptors, and to simultaneously introduce the biotin handle into the covalent complex. This allows the isolation and/or identification of the intact or subsequently fragmented complex using suitable avidin derivatives.

None of the compounds which are the object of the present invention has been described for the use in the study of protein-macrolide interactions at the molecular level.

In one aspect of the present invention, the conjugates of Formula I, and pharmaceutically acceptable salts, prodrugs, and solvates thereof, are represented as shown below:

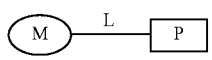

I wherein M represents a macrolide subunit possessing the property of accumulation in inflammatory cells, P represents a biotin subunit or subunit containing biotin and photo-affinity group and L represents a linker covalently linking M and P.

Suitable macrolide subunits for the hybrid compounds of the present invention can be selected without limitation from multi-member lactonic ring molecules, wherein "member" refers to the carbon atoms or heteroatoms in the ring, and "multi" is a number greater than about 10, preferably from 10 to about 50, more preferably 12-, 14-, 15-, 16-, 17- and 18-member lactonic ring macrolides. 14- and 15-member ring macrolide subunits are particularly preferred, with azithromycin and its derivatives and erythromycin and its derivatives being most preferred.

More specific nonlimiting examples of molecules from which the macrolide subunit can be selected are the following:
(i) Macrolide antibiotics, including azalides, for example erythromycin, dirithromycin, azithromycin, 9-dihydro-9-deoxo-9a-aza-9a-homoerythromycin, HMR 3004, HMR 3647, HMR 3787, josamycin, erythromycylamine, ABT 773 flurithromycin, clarithromycin, tylosin, tilmicosin, oleandomycin, desmycosin, CP-163505, roxithromycin, miocamycin and rokitamycin and derivatives thereof, such as ketolides (e.g., 3-ketone), lactams (e.g., 8a-, or 9a-lactams) and derivatives lacking one or more sugar moieties.
(ii) Macrolide immunosuppressants, such as FK 506, cyclosporin, amphotericin and rapamycin;
(iii) Macrolide antifungals with host cell inhibitory properties, such as bafilomycins, concanamycin, nystatin, natamycin, candicidin, filipin, etruscomycin, trichomycin.

DETAILED DESCRIPTION OF THE INVENTION

Methodologies for the synthesis of the above macrolides not commercially available and synthetic manipulation of macrolides in general are known to those of ordinary skill in the art, or may be found in: Denis A. et al. Bioorg. & Med. Chem. Lett 1999, 9, 3075-3080; Agouridas C. et al. J. Med. Chem. 1998, 41, 4080-4100; and EP-00680967 (1998); Sun Or Y. et al. J. Med. Chem. 2000, 43, 1045-1049; U.S. Pat. No. 0,574,7467 (1998); McFarland J. W. et al. J. Med. Chem. 1997, 40, 1041-1045; Denis A. at al. Bioorg. & Med. Chem. Lett. 1998, 8, 2427-2432; WO-09951616 (1999); Lartey et al. J Med. Chem. 1995, 38, 1793-1798; EP 0984019; WO 98/56801, each of which are herein incorporated by reference in their entirety.

Additional suitable macrolides are known, some being disclosed in Bryskier, A. J. et al. *Macrolides, Chemistry, Pharmacology and Clinical Use*; Arnette Blackwell: Paris, 1993, pp 485-491, 14(R)-hydroxyclarithromycin, erythromycin-11,12-carbonate, tri-O-acetyloleandomycin, spiramycin, leucomycin, midecamycin, rasaramycin incorporated by reference in its entirety; in Ma, Z. et al. *Current Medicinal Chemistry-Anti-Infective Agents,* 2002, 1, 15-34; also incorporated by reference in its entirety pikromycin, narbomycin, HMR-3562, CP-654743, CP-605006, TE-802, TE-935, TE-943, TE-806, 6,11-bridged ketolides, CP-544372, FMA-199, A-179461; and in Romo, D. et al. *J. Am. Chem. Soc.* 1998, 120; 12237-12254; also incorporated by reference in its entirety. See, in particular the structures and derivatives for 14- and 16-member ring macrolides at pp 487-491 of Bryskier, et al., and the various ketolide derivatives and syntheses in Ma et al., notably in all the structure tables and all the reaction schemes. All these macrolides after being conjugated to subunit P are within the scope of the present invention. The foregoing specifically named or referenced macrolide compounds are commercially available or methods for their syntheses are known.

In preferred embodiments, this invention relates to the use of compounds, represented by the Formula I, and salts, prodrugs and solvates thereof, wherein M specifically represents a 14- or 15-member lactonic ring macrolide subunit most preferably represented by the Formula II:

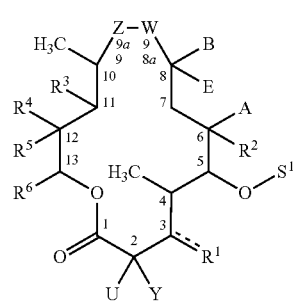

II wherein
(i) Z and W independently are

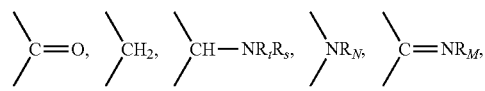

or a bond, wherein
R$_t$ and R$_s$ independently are H or alkyl (preferably methyl or H);
R$_M$ is OH, OR$^p$, alkoxy or substituted alkoxy (in either Syn or Anti configurations or mixtures thereof)
R$_N$ is H, R$^p$, alkyl, alkenyl, alkynyl, alkoxy, alkoxyalkyl, or —C(=X)—NR$_t$R$^s$; and
X is O or S;
provided that Z and W cannot both simultaneously be

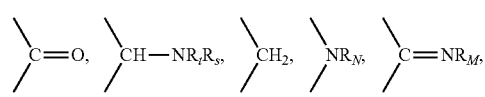

or a bond,
(ii) U and Y are independently H, halogen, alkyl, or hydroxyalkyl (preferably H, methyl, or hydroxymethyl);
(iii) R$^1$ is hydroxy, OR$^p$, —O—S$^2$, or =O;
(iv) S$^1$ is H or a sugar moiety at position C/5 (e.g., a desosamine group) of the formula:

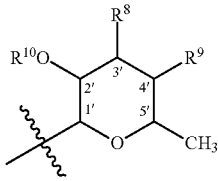

wherein
$R^8$ and $R^9$ are both hydrogen or together form a bond, or $R^9$ is hydrogen and $R^8$ is —N(CH$_3$)$R^y$, wherein
  $R^y$ is $R^p$, $R^z$ or —C(O)$R^z$, wherein $R^z$ is hydrogen or cycloalkyl (preferably cyclohexyl) or alkyl (preferably a $C_1$-$C_7$ alkyl) or alkenyl (preferably $C_2$-$C_7$-alkenyl) or alkynyl (preferably $C_2$-$C_7$-alkynyl) aryl or heteroaryl or alkyl substituted with $C_2$-$C_7$ alkyl, $C_2$-$C_7$ alkenyl, $C_2$-$C_7$ alkynyl, aryl or heteroaryl ($R^y$ is preferably hydrogen, methyl, ethyl, n-propyl, i-propyl, n-butyl, —C(O)CH$_3$, —CH$_2$-phenyl, or cyclohexyl);
$R^{10}$ is hydrogen or $R^p$;
(v) $S^2$ sugar moiety (e.g., is a cladinosyl group) of the formula

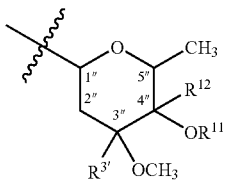

wherein $R^{3'}$ can be H or methyl and $R^{11}$ is hydrogen or $R^p$, —C(O)(CH$_2$)$_q$NR$^4$R$^6$, or O—$R^{11}$ is a group that with $R^{12}$ and with C/4" carbon atom forms a >C=O or epoxy group; $R^{12}$ is hydrogen or a group that with O—$R^{11}$ and with C/4" carbon atom forms a >C=O or epoxy group, wherein q has the meaning of an integer from 1 to 6;
(vi) $R^2$ is H, hydroxy, O$R^p$ group, alkoxy (preferably $C_1$-$C_4$ alkoxy, most preferably methoxy) or substituted alkoxy;
(vii) A is H or methyl;
(viii) B is methyl or epoxy;
(ix) E is H or halogen (preferably fluorine);
(x) $R^3$ is hydroxy, O$R^p$ group or alkoxy (preferably $C_1$-$C_4$ alkoxy, most preferably methoxy), substituted alkoxy or $R^3$ is a group that can combine with $R^5$ to form a "bridge" (e.g., a cyclic carbonate or carbamate) or if W or Z is

$R^3$ is a group that can combine with W or Z to form a "bridge" (e.g., a cyclic carbamate);
(xi) $R^4$ is $C_1$-$C_4$ alkyl (preferably methyl);
(xii) $R^5$ is H, hydroxy, O$R^p$ group, $C_1$-$C_4$ alkoxy, substituted alkoxy or a group that may combine with $R^3$ to form a bridge (e.g., a cyclic carbonate or carbamate);
(xiii) $R^6$ is H or $C_1$-$C_4$ alkyl (preferably methyl or ethyl);
wherein the subunit M has a linkage site through which it is linked to the subunit S via the linking group L, the linkage site being at one or more of the following:
any reactive hydroxy, N, or epoxy group located on $S^1$, $S^2$, or an aglycono oxygen if $S^1$ or $S^2$ is cleaved off;

a. a reactive >N—$R_N$ or —NR$_r$R$_s$, or =O group located on Z or W;
b. a reactive hydroxy group located at any one of $R^1$, $R^2$, $R^3$, and $R^5$;
c. any other group that can be first derivatized to a hydroxy or —NR$_r$R$_s$ group and then linked to K

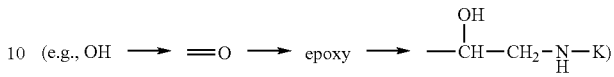

wherein K is the part of the linking molecule L.
One or more $R^p$ groups may be independently present in the macrolide subunit of Formula II, wherein $R^p$ represents a protective group which may be selected from alkyl (preferably methyl), alkanoyl (preferably acetyl), alkoxycarbonyl (preferably methoxycarbonyl or tert-butoxycarbonyl), aryl-methoxycarbonyl (preferably benzyloxycarbonyl), aroyl (preferably benzoyl), arylalkyl (preferably benzyl), alkylsilyl (preferably trimethylsilyl) or alkylsilylalkoxyalkyl (preferably trimethylsilylethoxymethyl).
Also preferred are semiglycone compounds according to formula II where $R^1$ and $R^1$ is hydroxyl and $S^1$ is a sugar moiety of the formula ($R^{10}$, $R^8$, $R^9$ are as previously defined):

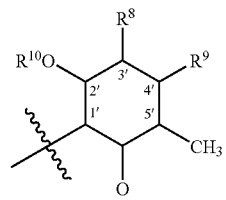
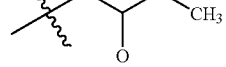

Also preferred are semiglycone compounds according to formula II where $S^1$ is H and $R^1$ is O—$S^2$ where $S^2$ is a sugar moiety of the formula ($R^{3'}$, $R^{11}$$R^{12}$ are as previously defined):

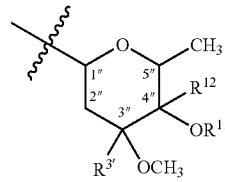

Also preferred are aglycone compounds according to formula II is wherein $S^1$ is hydrogen and $R^1$ is hydroxyl.
The Linker L
L is a spacer or linker molecule that can be any type of spacer molecule providing the required spacing. For example, L can be selected to be a linking group represented by the Formula IIIA or IIIB:

$$X^1—(CH_2)_m—X^2 \quad\quad\quad IIIA$$

$$X^1—(CH_2)_m-Q-(CH_2)_n—X^2 \quad\quad\quad IIIB$$

wherein
$X^1$ is selected from: —CH$_2$—, —CH$_2$—NH—, —C(O)—, —OC(O)—, =N—O—, —OC(O)NH— or —C(O)NH—;
$X^2$ is selected from: —NH—, —CH$_2$—; —NHC(O)—, —C(=O)—, —O— or —OC(O)—;
Q is —NH—, —CH$_2$— or —S—S—;
wherein each —CH$_2$— or —NH— group is optionally substituted by $C_1$-$C_7$-alkyl, $C_2$-$C_7$-alkenyl, $C_2$-$C_7$-alkynyl, C(O)$R^x$, C(O)O$R^x$, C(O)NH$R^x$ wherein $R^x$ may be $C_1$-$C_7$-alkyl, aryl or heteroaryl;

the symbols m and n are independently a whole number from 0 to 8 with the proviso that if Q=NH; n cannot be zero.

The foregoing definition of the linking group is preferred not only for conjugates of P and macrolides of Formula II but for any conjugate within Formula I. Other linking groups can be used as long as they provide the necessary spacer. Preferred linker molecules are those having a length of 1-60 carbon atoms (not counting heteroatoms in the chain) and those having a length of 2-20 carbon atoms are most preferred. Linkage of L to the macrolide moiety can be effected either through the ring nitrogen atom at position 9a or through the hydroxy group at position 11 and position 6 or through the 2' hydroxy or the 3' amino group of the desozamine sugar moiety or through the 4" hydroxy group of the cladinose sugar or if the M moiety is aglycone or missing one of the desozamine and cladinose sugar groups, through the OH group created at position 5 or 3 of the macrolide ring. The linker can serve to link one subunit of the Formula I with the other, as is well-known in the art.

The Subunit P

P is a photoaffinity subunit that contains a group that can be chemically crosslinked with electromagnetic radiation and a biotin or an iminobiotin. Known derivatives of biotin or iminobiotin contained in a photoaffinity subunit are also contemplated in the present invention.

In a preferred embodiment, P represents a photoaffinity group containing a biotin or iminobiotin subunit that can be represented by the substructure IV:

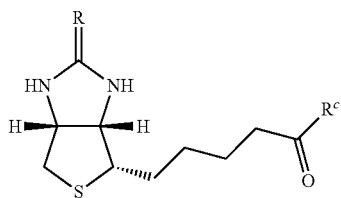

IV wherein $R^c$ is the covalent link chain L, e.g., at $X^2$;

R is O (biotin) or NH (iminobiotin);

or P represents a subunit containing biotin and a photoaffinity group that can be represented by the substructure V:

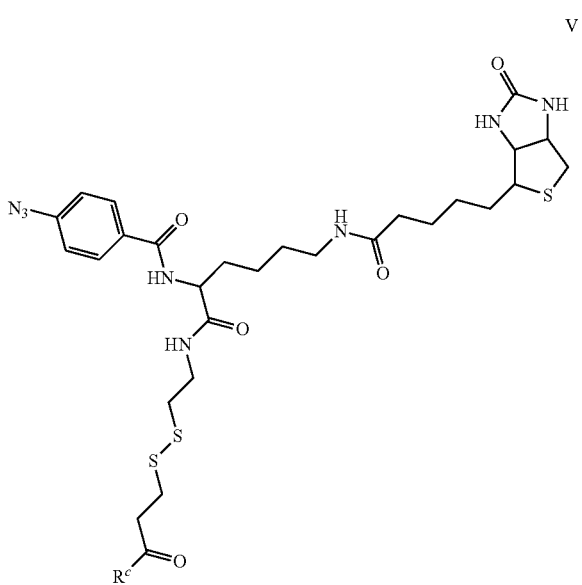

V wherein $R^c$ is a covalent link with chain L, e.g., at $X^2$;

Other suitable photoreactive groups are described, for example, in S. A. Fleming, Tetrahedron, 1995, 51, 12479-12520 (Chemical Reagents in Photoaffinity Labeling), incorporated by reference. They include without limitation: phenyl azides, fluorophenylazides, nitrofluorophenylazides, para-azidoaniline, para-azidobenzoyl, aryl diazirines, diazoketone, benzophenone.

Bold-faced bonds in formulas contained herein denote bonds raised above the paper level; dash-drawn bonds denote bonds below the paper level, whereas broken lines represent a bond that may be either below or above the paper level. Parallel full and broken lines represent either a single or a double bond. Unless explicitly stated elsewhere herein, the following terms have the meanings ascribed to them below:

"Alkyl" means a linear or branched saturated monovalent hydrocarbon radical of one to ten carbon atoms, more preferably one to six carbon atoms The preferred straight-chain or branched-chain alkyls include methyl, ethyl, propyl, iso-propyl, butyl, sec-butyl and tert-butyl. Methyl is most preferred. Alkyl groups may be substituted with one up to five substituents including halogen (preferably fluorine or chlorine), hydroxy, alkoxy (preferably methoxy or ethoxy), acyl, acylamino cyano, amino, N—($C_1$-$C_4$)allylamino (preferably N-methylamino or N-ethylamino), N,N-di($C_1$-$C_4$-alkyl)amino (preferably dimethylamino or diethylamino), aryl (preferably phenyl) or heteroaryl, thiocarbonylamino, acyloxy, amino, amidino, alkyl amidino, thioamidino, aminoacyl, aminocarbonylamino, aminothio-carbonylamino, aminocarbonyloxy, aryl, heteroaryl, aryloxy, aryloxyaryl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, cycloalkoxy, heteroaryloxy, heterocyclyloxy, and oxycarbonylamino. Such substituted alkyl groups are within the present definition of "alkyl." The present definition of allyl carries over to other groups having an alkyl moiety such as alkoxy.

"Alkenyl" means a linear or branched monovalent hydrocarbon radical of two to ten and preferably two to six carbon atoms which has at least one double carbon-carbon bond. Alkenyl groups may be substituted with the same groups as alkyl and such optionally substituted alkenyl groups are encompassed within the term "alkenyl." Ethenyl, propenyl, butenyl and cyclohexenyl are preferred.

"Alkynyl" means a linear or branched monovalent hydrocarbon radical, having a straight-chain or a branched-chain of two to ten, and preferably two to six carbon atoms and containing at least one and preferably no more than three triple carbon-carbon bonds. Alkynyl groups can be substituted with the same groups as alkyl, and the substituted groups are within the present definition of alkynyl. Ethynyl, propynyl and butynyl groups are preferred.

"Cycloalkyl" means a cyclic group having 3-8 carbon atoms having a single ring optionally fused to an aryl or heteroaryl group. Cycloalkyls may optionally be fused to a saturated ring. The cycloalkyl groups can be substituted as specified for "aryl" below, and the substituted cycloalkyl groups are within the present definition of "cycloalkyl". Preferred cycloalkyls are cyclopropyl, cyclobutyl, cyclopentyl, cyclohexyl and cycloheptyl. Also included are alkyl cycloalkyls where the cycloalkyl is attached through an alkyl chain having 1-6 carbons.

"Aryl" means an unsaturated aromatic carbocyclic group having 6-14 carbon atoms having a single ring such as phenyl or multiple fused rings such as naphthyl. Aryl may optionally be further fused to an aliphatic or aryl group or can be substituted with one or more substituents such as halogen (fluorine, chlorine and/or bromine), hydroxy, $C_1$-$C_7$ alkyl, $C_1$-$C_7$ alkoxy or aryloxy, $C_1$-$C_7$ alkylthio, arylthio, alkylsulfonyl, cyano, primary or nonprimary amino, haloalkyl, or alkylamino.

"Heteroaryl" means a monocyclic or a bicyclic aromatic hydrocarbon ring having from 2 to 10 carbon atoms and from 1 to 4 heteroatoms, such as O, S or N. The heteroaryl ring may optionally be fused to another heteroaryl, aryl or aliphatic cyclic group. Examples of this type are furan, thiophene, pyrrole, imidazole, indole, pyridine, oxazole, thiazole, pyrrole, pyrazole, tetrazole, pyrimidine, pyrazine and triazine, with furan, pyrrole, pyridine and indole being preferred. The term includes groups that are substituted with the same substituents as specified for aryl above.

"Heterocyclic" means a saturated or unsaturated group having a single or multiple rings and from 1 to 10 carbon atoms and from 1-4 heteroatoms selected from nitrogen, sulphur or oxygen, wherein in a fused ring system the other ring or rings can be aryl or heteroaryl. Heterocyclic groups can be substituted as specified for alkyl groups and the thus substituted heterocyclic groups are within the present definition.

"Electromagnetic radiation" as used herein refers to energy waves of the electromagnetic spectrum including, but not limited to, X-ray, ultraviolet, visible, infrared, far infrared, microwave, radio-frequency, sound and ultrasound waves. Preferably, the electromagnetic radiation will comprise visible (i.e., having a wavelength of at least approximately $4.0 \times 10^{-5}$ cm to about $7.0 \times 10^{-5}$ cm.) or ultraviolet (i.e. having a wavelength of at least approximately $1.0 \times 10^{-6}$ cm but less than $4.0 \times 10^{-5}$ cm) light. The present invention also encompasses pharmaceutically acceptable salts of the present compounds. Pharmaceutically suitable salts of the compounds of the present invention include salts with inorganic acids (e.g. hydrochloric, hydrobromic, phosphoric, metaphosphoric, nitric or sulfuric acid) or organic acids (e.g. tartaric, acetic, methane-sulfonic, trifluoroacetic, citric, maleic, lactic, fumaric, benzoic, succinic, methanesulfonic, oxalic and p-toluenesulfonic acids).

The present invention also encompasses prodrugs of the Formula I compounds, i.e., compounds which release an active parent drug according to Formula (I) in vivo when administered to a mammalian subject. Prodrugs of a compound of Formula I are prepared by modifying functional groups present in the compound of Formula I in such a way that the modifications may be cleaved in vivo to release the parent compound. Prodrugs include compounds of Formula I wherein a hydroxy, amino, or carboxy group of a Formula I compound is bonded to any group that may be cleaved in vivo to regenerate the free hydroxyl, amino or carboxy group, respectively. Examples of prodrugs include, but are not limited to esters (e.g., acetate, formate, and benzoate derivatives) of compounds of Formula I, or any other derivative which upon being brought to the physiological pH or through enzyme action is converted to the active parent drug.

The present invention also encompasses solvates (preferably hydrates) of the compounds of Formula I or their salts.

The compounds of the Formula I have one or more chirality centers and, depending on the nature of individual substituents, they can also have geometrical isomers. Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has a chiral center, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomer respectively). A chiral compound can exist as either an individual enantiomer or as a mixture of enantiomers. A mixture containing equal proportions of the enantiomers is called a "racemic mixture". The present invention encompasses all individual isomers of compounds of Formula I. The description or naming of a particular compound in the specification and claims is intended to include both individual enantiomers and mixtures, racemic or otherwise, thereof. Methods for the determination of stereochemistry and the resolution of stereoisomers are well-known in the art.

The present invention also encompasses stereoisomers of the syn-anti type, and mixtures thereof encountered when an oxime or similar group is present. The group of highest Cahn Ingold Prelog priority attached to one of the terminal doubly bonded atoms of the oxime, is compared with hydroxyl group of the oxime. The stereoisomer is designated as Z (zusammen=together) or Syn if the oxime hydroxyl lies on the same side of a reference plane passing through the C=N double bond as the group of highest priority; the other stereoisomer is designated as E (entgegen=opposite) or Anti.

In one embodiment, where Z or W of Formula I is >C=NR''' and R''' is OH, OR$^9$, or a substituted alkoxy, the compound is predominantly the syn isomer. In another embodiment, the compound is predominantly the anti isomer. In yet another embodiment, the compound is a 50/50 mixture of the two isomers, or alternatively a mixture such as 60/40, 70/30, 80/20, or 90/10 syn to anti or alternatively anti to syn.

Specific conjugates of Formula I that may be used according to the present invention are:

compound 1

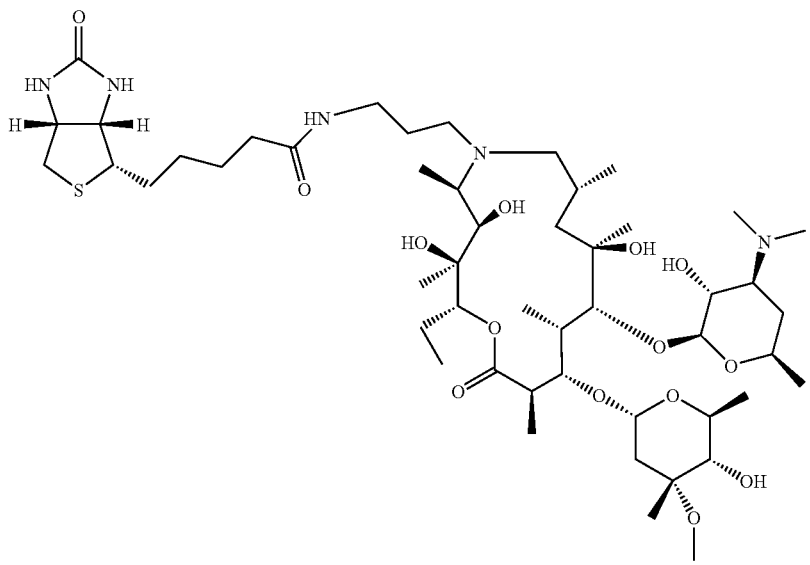

compound 2
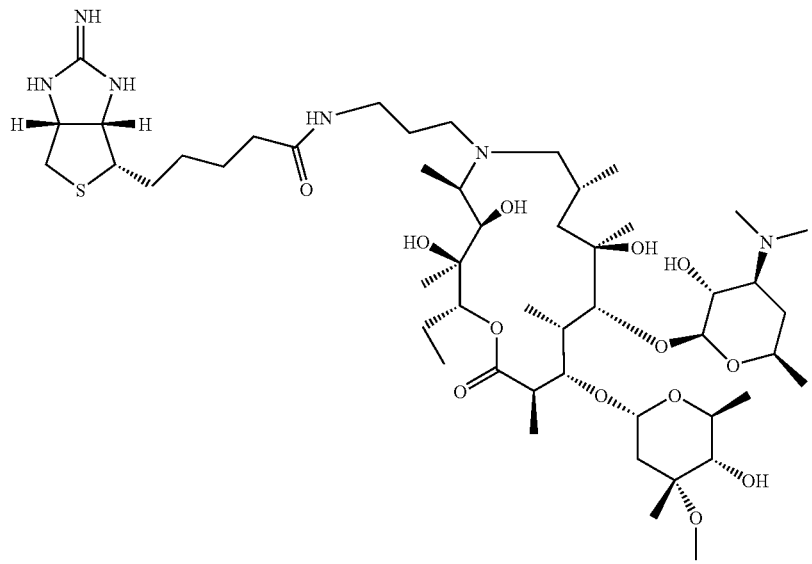
compound 3
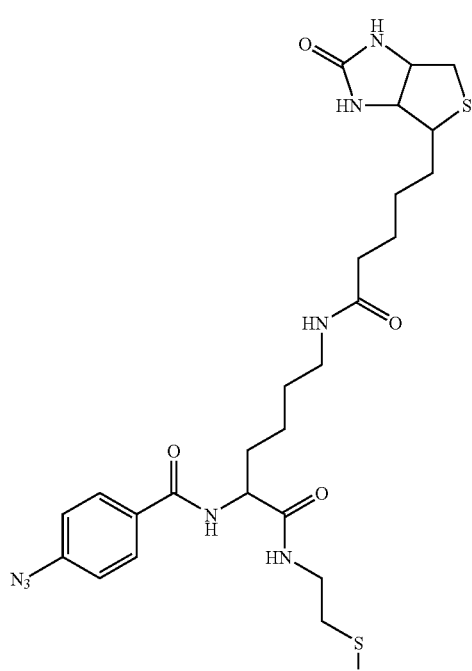

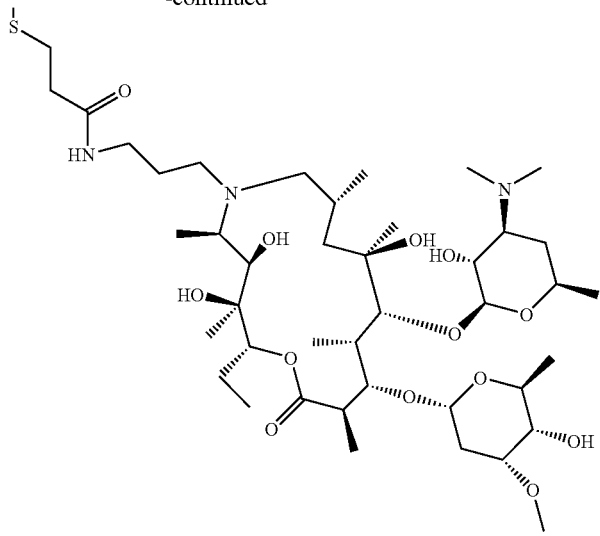
compound 4
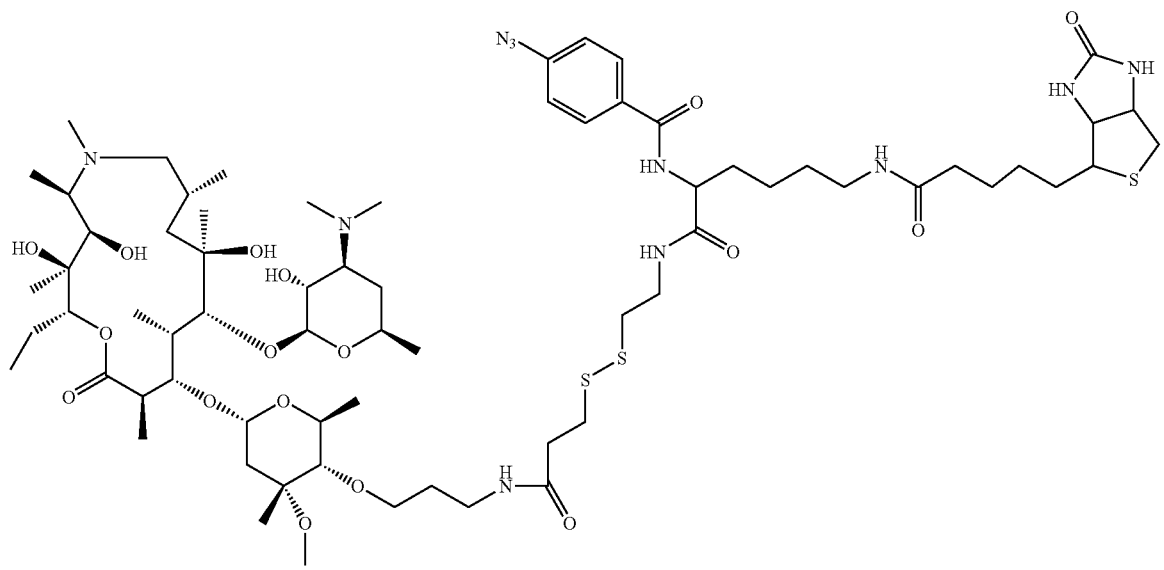
compound 5
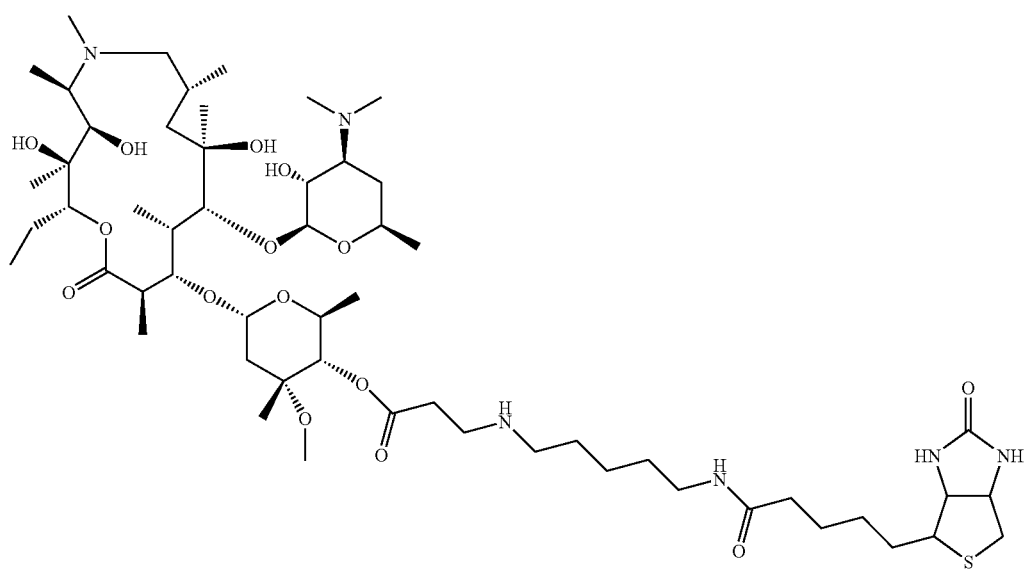

compound 6
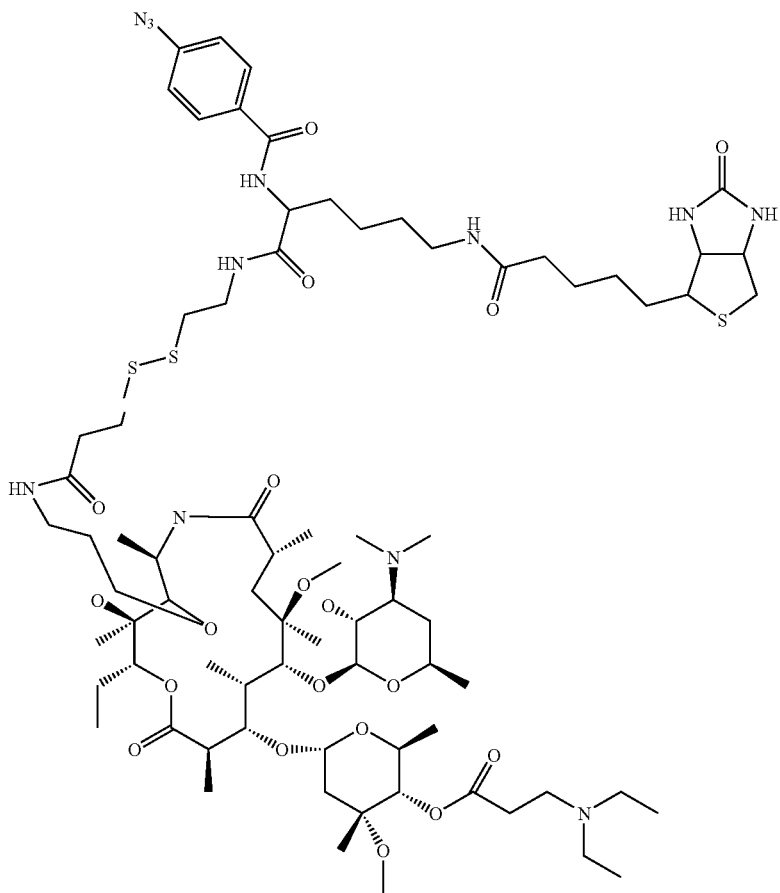
compound 7
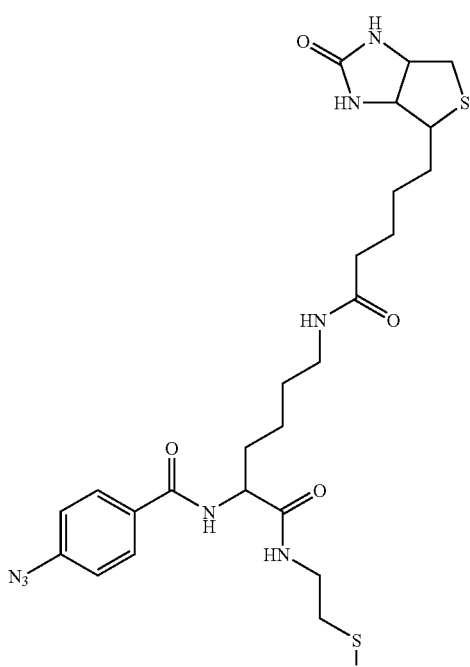

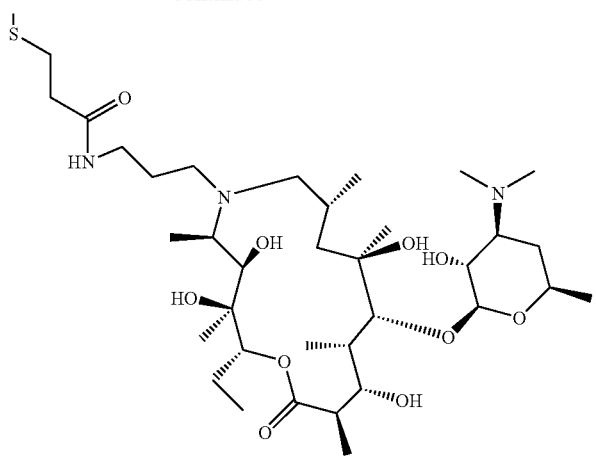
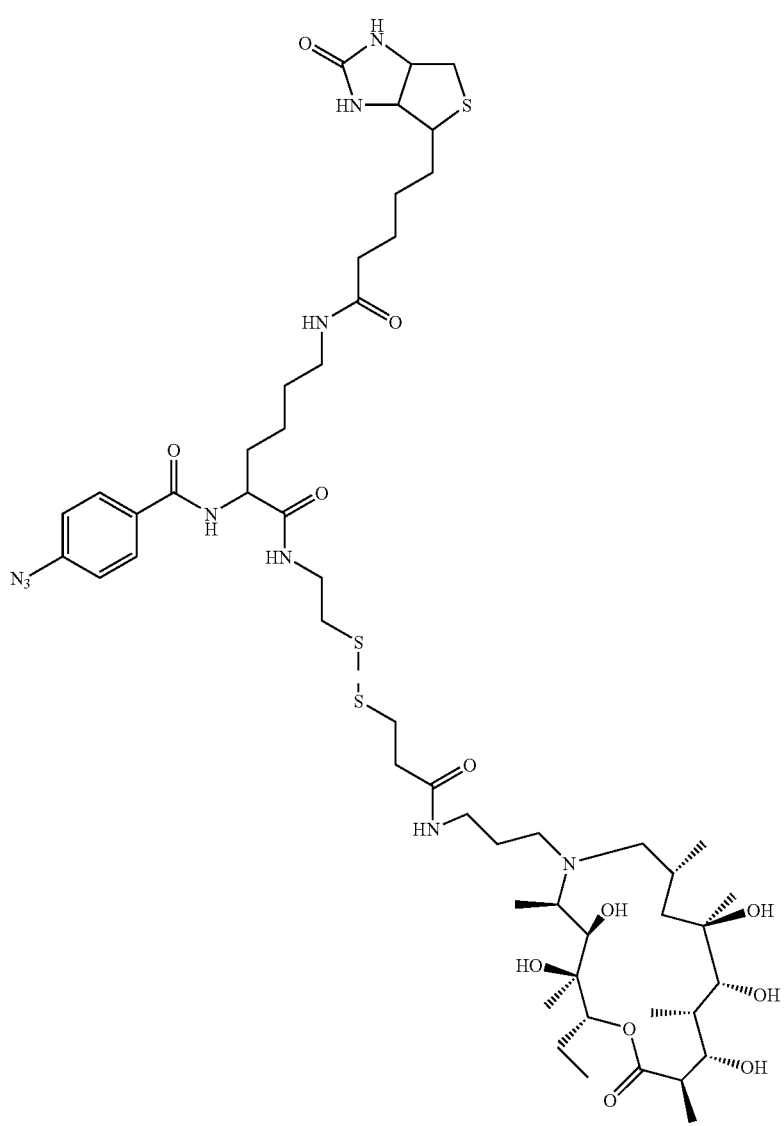
compound 8

-continued
compound 9
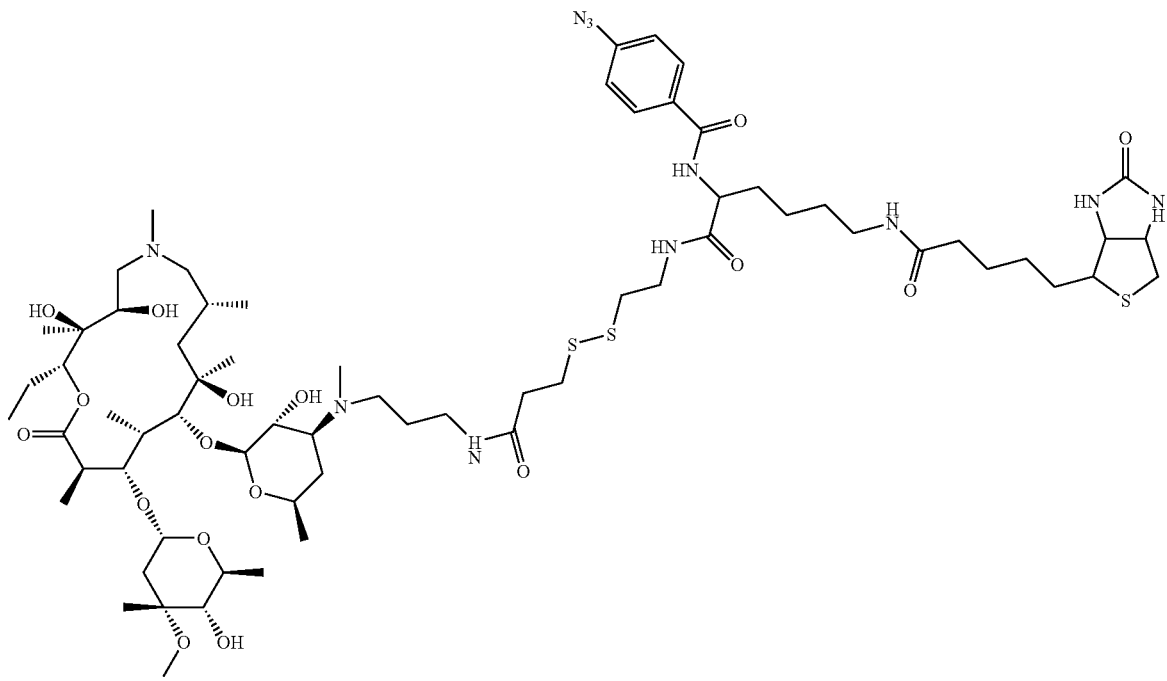
compound 10
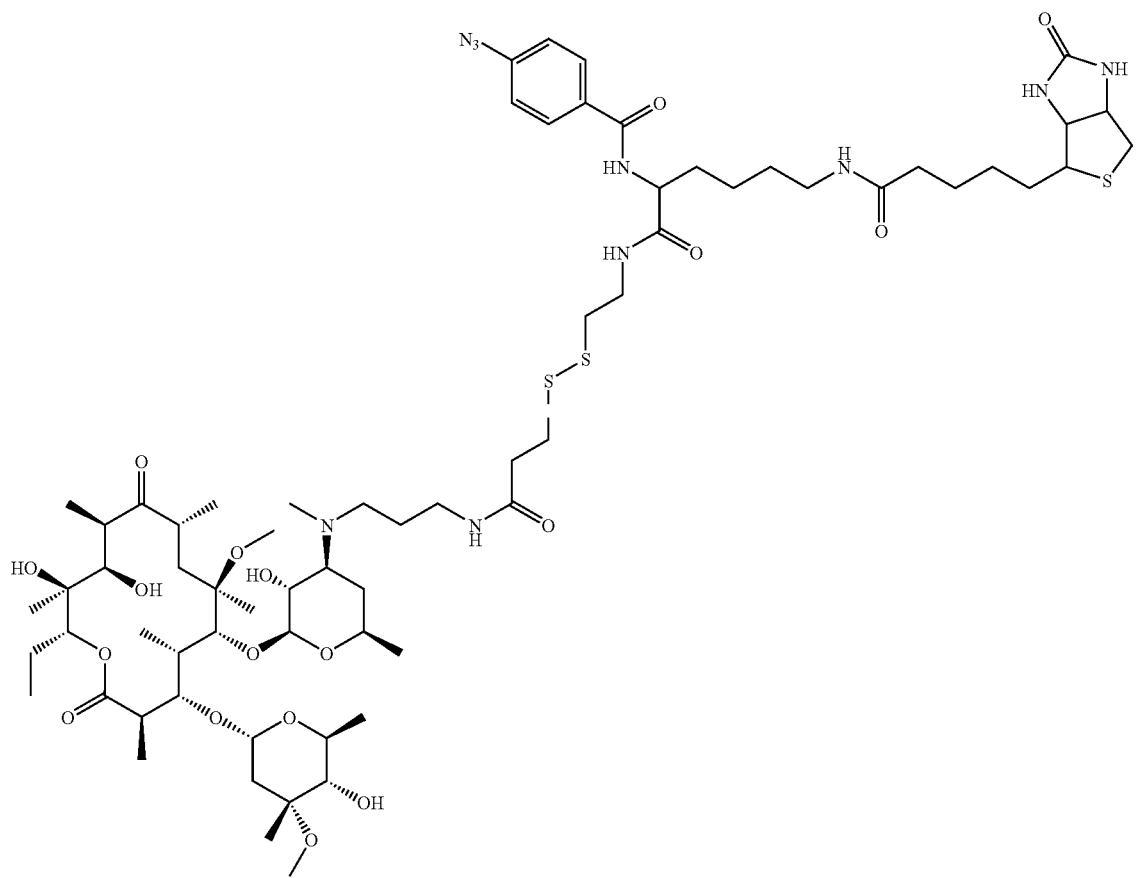

compound 11
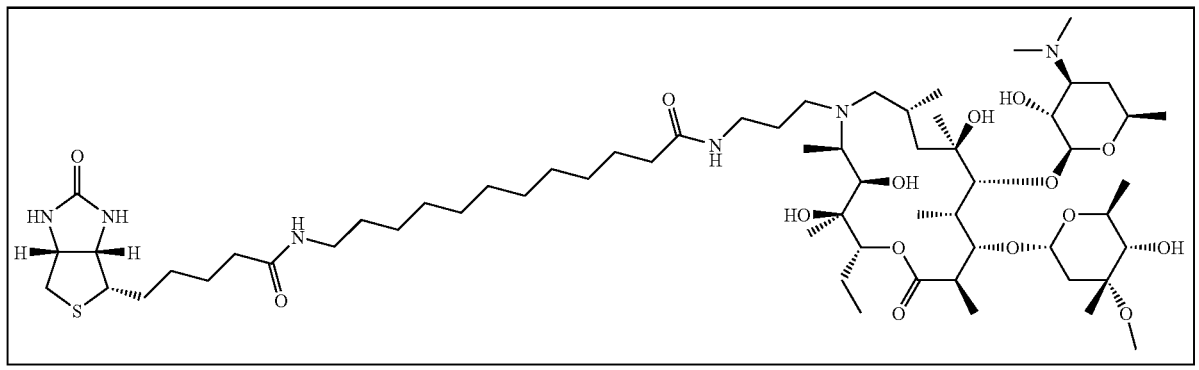
compound 12
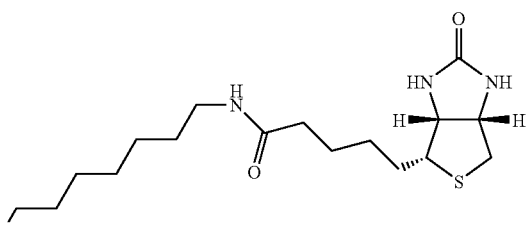
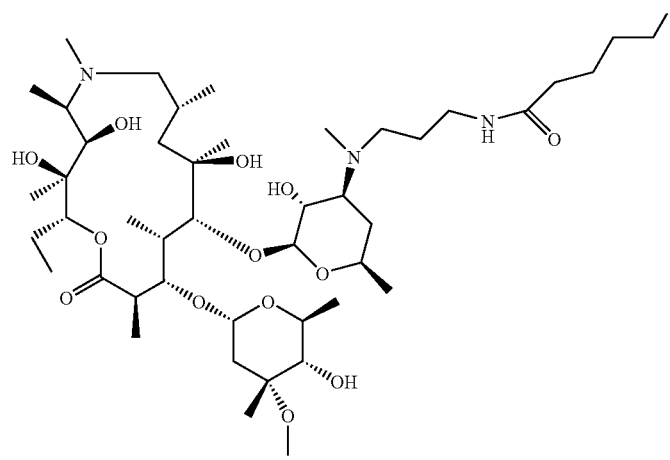
compound 13
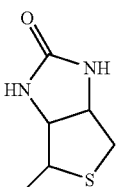
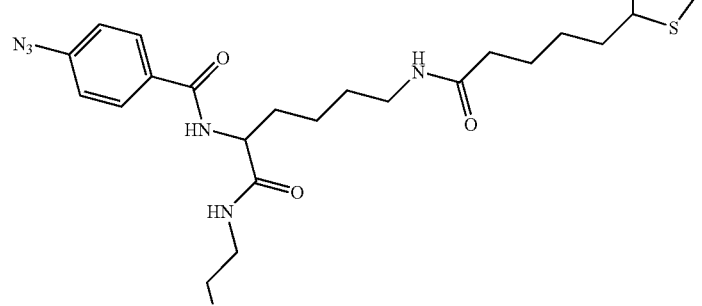

-continued

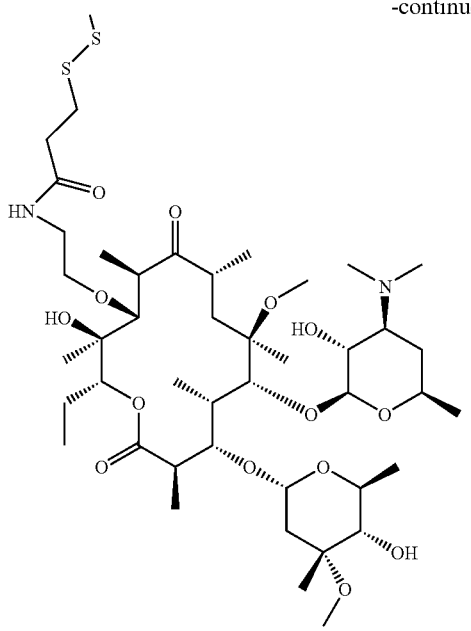

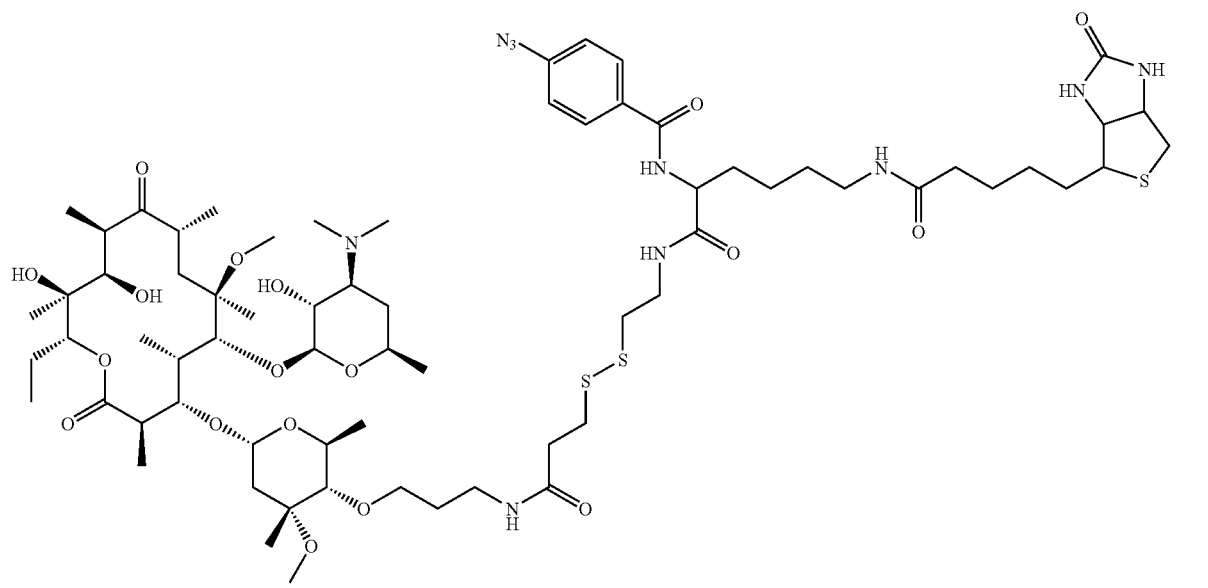

compound 14

The linkage site is preferably at position C/3; or through the amino group at position C/3' of $S^1$ sugar or at position C/11 or at W or Z, or through position C/4" of $S^2$ sugar.

A further aspect of the present invention relates to processes for the preparation of compounds represented by Formula I. Generally, the compounds of Formula I may be obtained in the following way: one end of the chain is first linked to the macrolide, and then the other end of the chain is linked to the P; or, one end of the chain is first linked to the P and then the other end of the chain to the macrolide, or finally, one moiety of the chain is linked to the macrolide, whereas the other moiety of the chain is linked to the P, with the free ends of the chain parts being then chemically linked to form the chain L.

It will be appreciated by those skilled in the art that it may be desirable to use protected derivatives of intermediates used in the preparation of the compounds of Formula I. Protection and deprotection of functional groups may be performed by methods known in the art. Hydroxyl or amino groups may be protected with any hydroxyl or amino protecting group, for example, as described in Green, T. W.; Wuts, P. G. M., *Protective Groups in Organic Synthesis*: John Wiley and Sons, New York, 1999. See also the discussion of protective groups in connection with Formula I above. The amino protecting groups may be removed by conventional techniques. For example, acyl groups, such as alkanoyl, alkoxycarbonyl and aroyl groups, may be removed by solvolysis, e.g., by hydrolysis under acidic or basic conditions. Arylmethoxycarbonyl groups (e.g., benzyloxycarbonyl) may be cleaved by hydrogenolysis in the presence of a catalyst such as palladium-on-charcoal.

More specifically, compounds within Formula I can be prepared by the following processes:

a) Compounds of Formula I, where $X^2$ is —NHC(O)—, can be formed by reacting a compound of Formula VI:

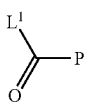

VI wherein L¹ represents a leaving group (such as hydroxy or sulfonated N-hydroxysuccinimide: sulfo-NHS), and a free amino group of a macrolide represented by Formula VIIa:

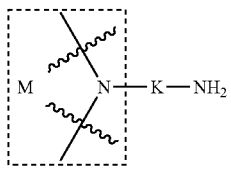

VIIa wherein K is the portion of the linking molecule L attached to the macrolide subunit.

The reaction is generally performed with acid derivatives which have the ability to activate the carboxylic acid group such as halogenides, mixed anhydrides and especially carbodiimides such as (3-dimethylaminopropyl)-3-ethyl-carbodiimide (EDC) and benzotriazoles. The reaction proceeds in the presence of a base, such as an organic base (e.g., triethylamine), at room temperature under an inert atmosphere, such as argon or nitrogen. The reaction may require several hours to several days to come to completion.

For example, when L is —K—NH₂ the compound of Formula I can be formed by derivatizing an >NH group on the macrolide ring to an >N—K—NH₂ group and reacting the derivatized macrolide with a compound of Formula VI as shown below.

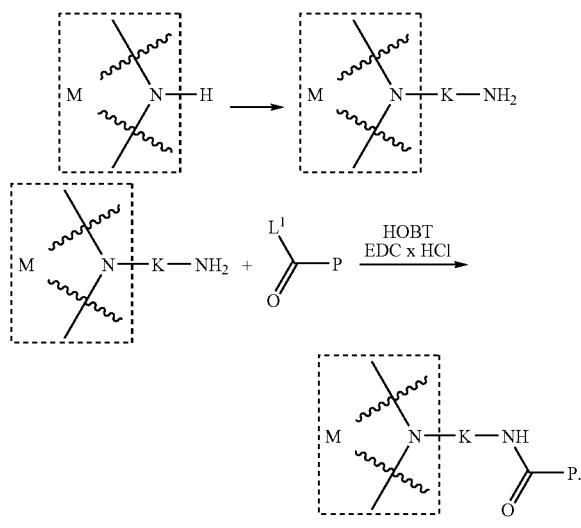

For example this process may be performed when the >NH group in the macrolide subunit of Formula II is attached at the C/3' or N/9a position.

Compound represented by Formula VI are commercially available or they can be derived from the subunit P by methods known in the art for addition reactions.

Preparation of the starting macrolide of Formula VIIa has been described in PCT HR 02/0001, incorporated by reference in its entirety. See also U.S. Pat. No. 4,474,768 and Bright, G. M. et al, *J. Antibiot.* 1988, 41, 1029-1047, each incorporated by reference in its entirety.

b) Compounds represented by Formula I, wherein X¹ is —OC(O)—, Q is —CH₂— or NH, and X² is —NH—, can be prepared by reacting a macrolide subunit represented by the formula

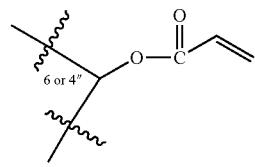

where 4" is the 4 position on a sugar S², such as a cladinose sugar, and subunit P having a free amino group represented by the formula:

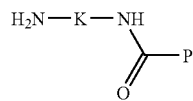

in a solvent, such as acetonitrile, to yield

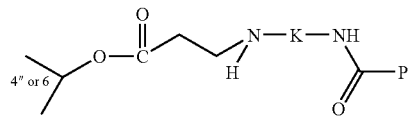

The derivatized subunit P (i.e., P—C(O)—NH—K—NH₂) may be formed by reacting an appropriate amine (having the linkage group —K—NH₂) with a carboxylic acid group of a subunit P.

c) Compounds represented by Formula I, where X¹ is —OC(O)NH— and X² is —NH—, can be prepared by reacting a macrolide subunit and a derivatized subunit P having a free amino group as shown below.

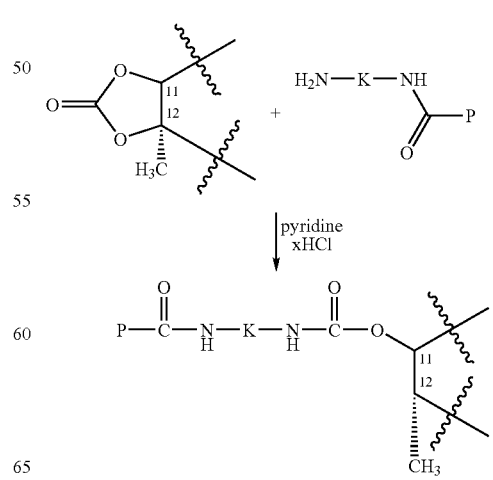

d) Compounds represented by Formula I, where $X^1$ is —OC(O)NH— and $X^2$ is —NH—, can be prepared by reacting a macrolide subunit and a derivatized subunit P having a free amino group as shown below.
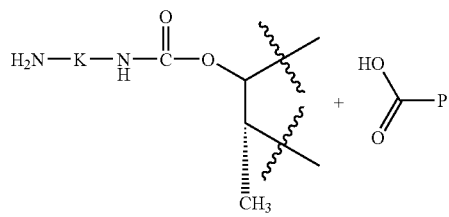
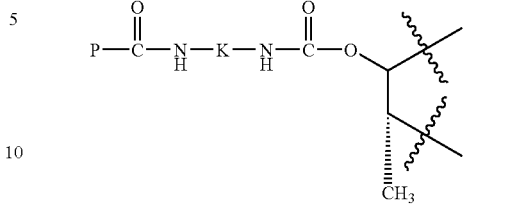
Compounds represented by Formula I (M-biotin-photoaffinity group) can be prepared also by reacting a macrolide subunit VIIa and Fmocbiocytin as shown below.
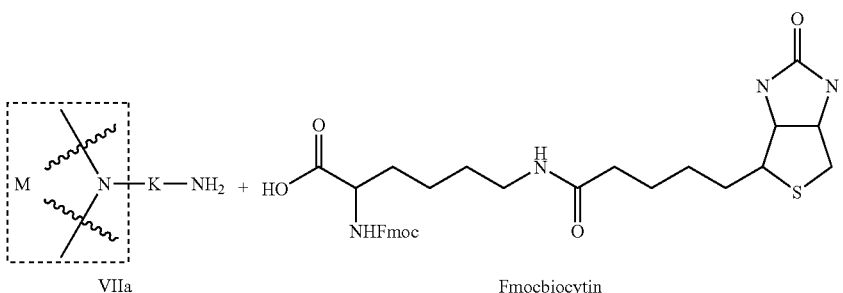
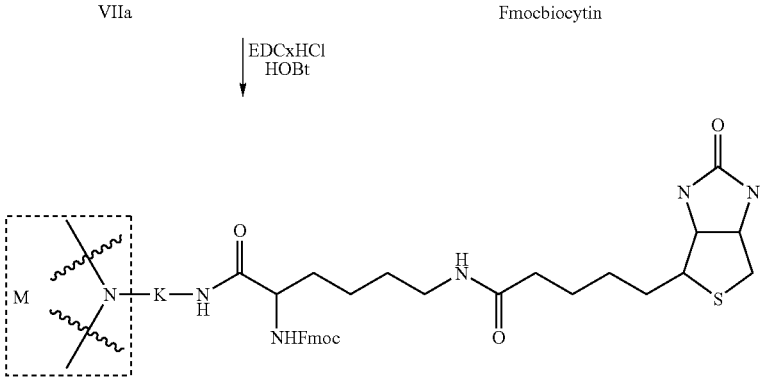
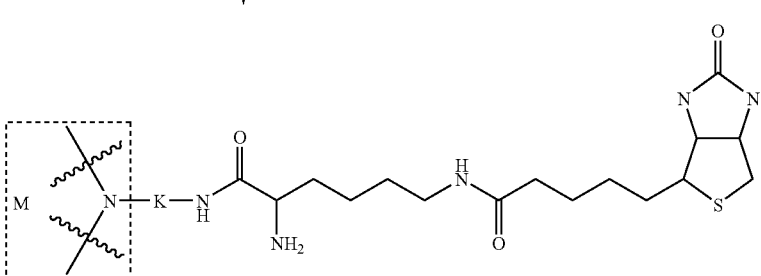
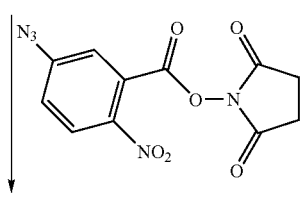

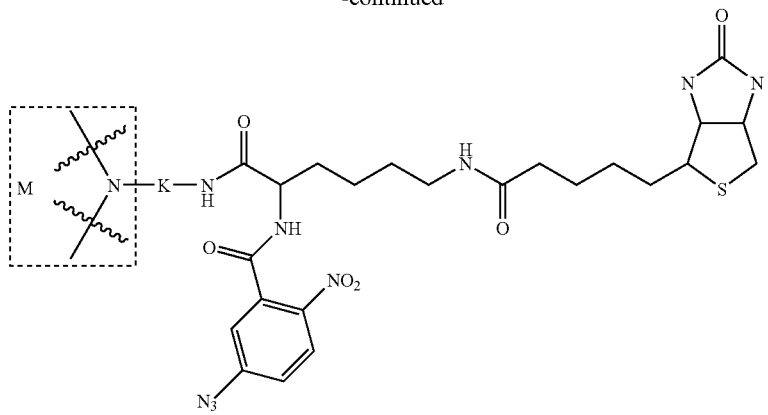

Fmocbiocytin (Nα-Fmoc-Nε-biotinyl-L-lysine) and 5-Azido-2-nitrobenzoic acid -N-hydroxysuccinimide ester are commercially available (Fluka).

The 16-membered ring macrolides are traditionally divided into sub-families based upon the substitution patterns of their aglycones. The principal prototypes of this family can be represented by leucomycin, spiramycin and tylosin.

Tylosin is a representative of 16-membered macrolides, which possesses a highly substituted aglycone with two double bonds (tylonolide) and a third saccharide substituent (β-D-mycinose) beta-D-mycosine in addition to the disaccharide attached to the 5-hydroxyl group. Hydrolysis of mycarose from disaccharide yielded desmycarosyl-tylosin (desmycosin).

Potential sites of modification in desmycosin:

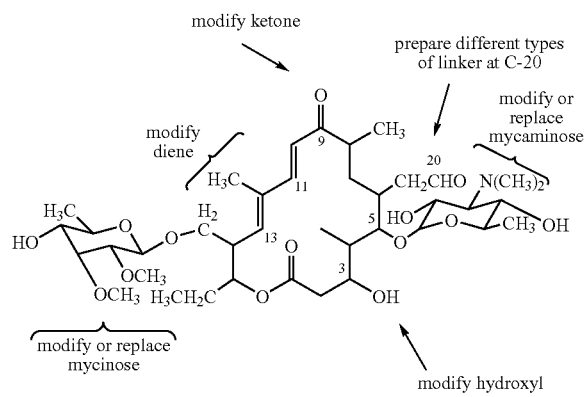

For example, a 16-membered ring macrolide hybrid could be prepared by reductive amination of the C-20 aldehyde group.

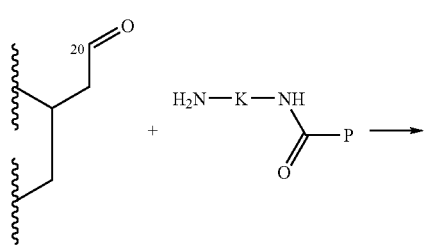

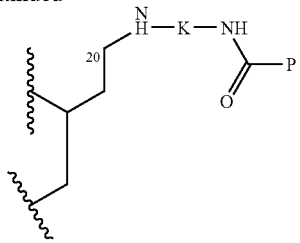

This reaction could be used also for 17-membered azalides like 8a-aza-homodesmycosins and its derivatives (such as di- and tetrahydro derivatives).

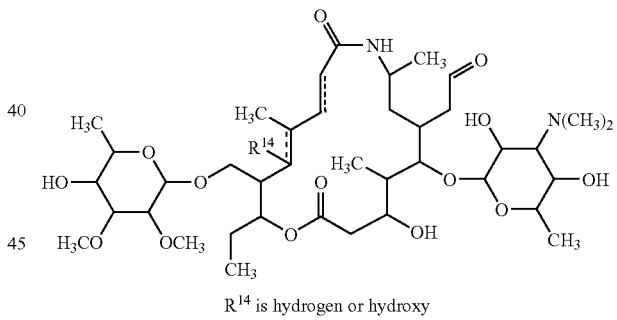

$R^{14}$ is hydrogen or hydroxy

The other possibilities in 16-membered ring macrolide derivatisation include transformations of double bonds by epoxidation, and cleaving the epoxy group with an appropriate reactant (such as diamines) to yield the reactant macrolide subunit (M-$CH_2$—NH—K—$NH_2$).

Additionally, the ketone in position 9 can be modified by hydroxylamine hydrochloride to yield oxime and then reduced to amine.

Targeting

The compounds from this invention are used for identification of target proteins i.e. proteins, peptides or polypeptides that interact with this compounds. It is known that target identification can be performed using the following approaches.

One of the approaches is phage display. In this approach phage particles expressing random polypeptide, cDNA or gene fragment libraries on their surface are incubated with immobilized or soluble compound. Individual phages are rescued through interaction of the protein or polypeptide with the compound and the proteins are identified by DNA sequences encoding them. A biotin or iminobiotin tag is used in this approach for immobilization of compounds on a solid support for example streptavidin coated 96 well plates or magnetic beads, or for capture in solution of formed phage-compound complex on streptavidin coated solid support.

Another approach uses affinity-based methods. Biotin or iminobiotin tagged compounds are allowed to bind to their target proteins from various sources, for example from cell lysates, plasma, urine etc. This may be done in solution, (i.e., by mixing the biotin or iminobiotin tagged compounds with the lysate, plasma, urine, etc.) or by mixing a streptavidin-containing solid matrix having the biotin or iminobiotin tagged compound immobilized on the surface with the solution, plasma, urine etc.

Specificity of target binding is improved by derivatization of compounds with a photoreactive group, for example an aryl-azide. In this approach, in addition to affinity binding, the compound covalently attaches to target protein through stimulating the photo-activated group with electromagnetic radiation. For complexes formed in solution, the streptavidin-containing matrix is then added to the covalently bound complex.

The compound-protein complexes are then isolated using the biotin or iminobiotin tag bound to streptavidin-containing solid matrix. Isolated proteins are identified, for example, by mass spectrometry.

The present invention is particularly useful since the binder proteins will not dissociate from the macrolide moiety during washing step, even when the macrolide-protein interactions are relatively weak. This advantage is due to the covalent bond between the photo-affinity group and the macrolide molecules (probes) that prevents dissociation of the targets (proteins) during the washing step. This approach presents a basis for identification of all targets, irrespective of their binding affinity (constant).

The compounds, process and method of the present invention will be better understood in connection with the following examples, which are intended as an illustration only and not limiting the scope of the invention. Various changes and modifications to the disclosed embodiments will be apparent to those skilled in the art and such changes and modifications including, without limitation, those relating to the chemical structures, substituents, derivatives formulations and/or methods of the invention may be made without departing from the spirit of the invention and the scope of the appended claims.

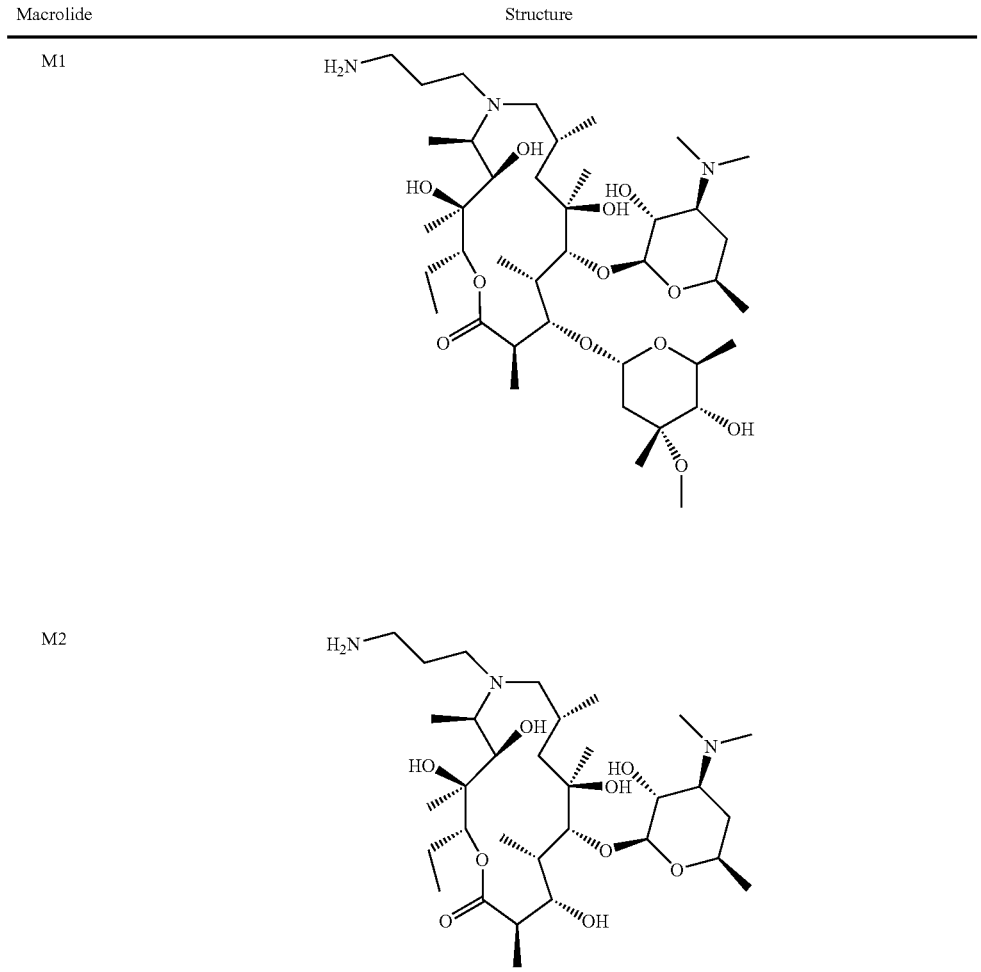

| Macrolide | EXPERIMENTAL Structure |
|---|---|
| M1 | |
| M2 | |

| Macrolide | Structure |
|---|---|
| M3 | 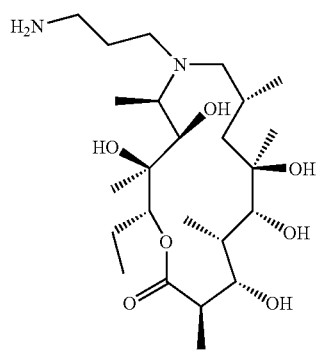 |
| M4 | 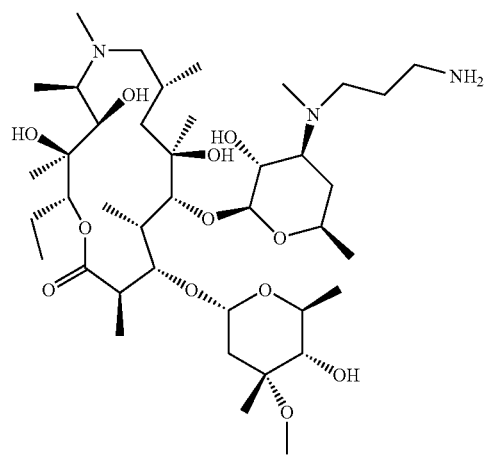 |
| M5 | 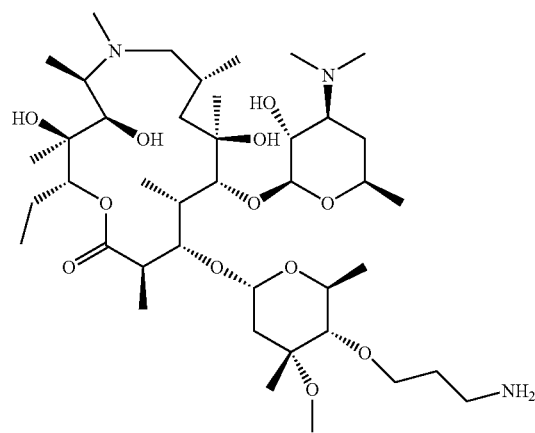 |

-continued
| Macrolide | Structure |
|---|---|
| M6 | 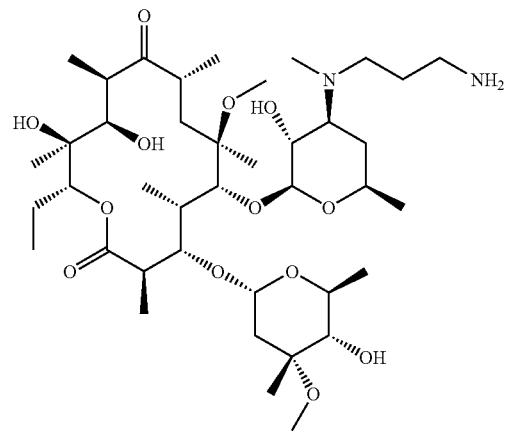 |
| M7 | 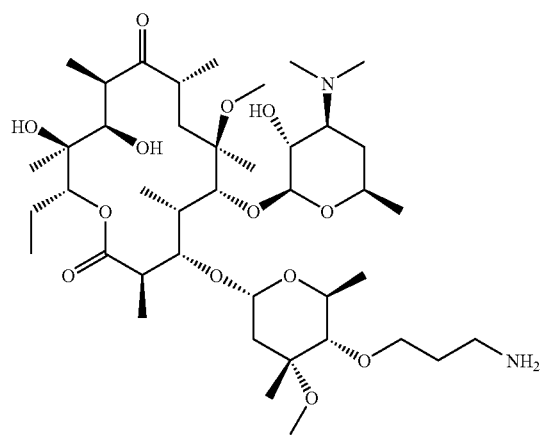 |
| M8 | 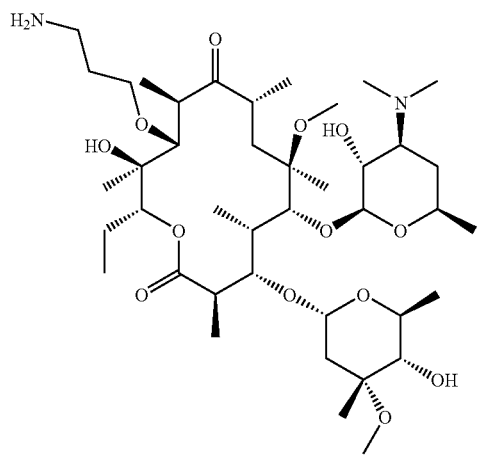 |

-continued
EXPERIMENTAL
| Macrolide | Structure |
|---|---|
| M9 | 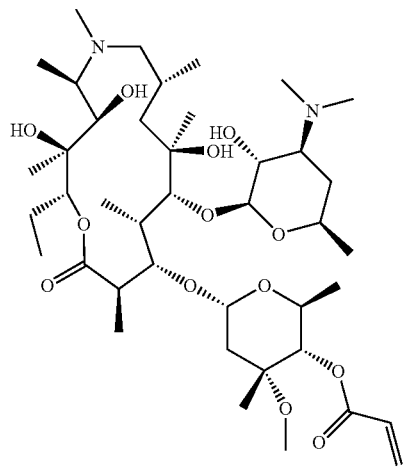 |
| M10 | 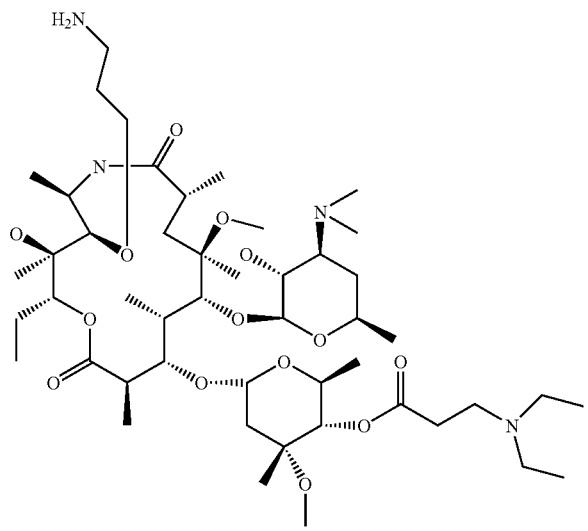 |
| M11 | 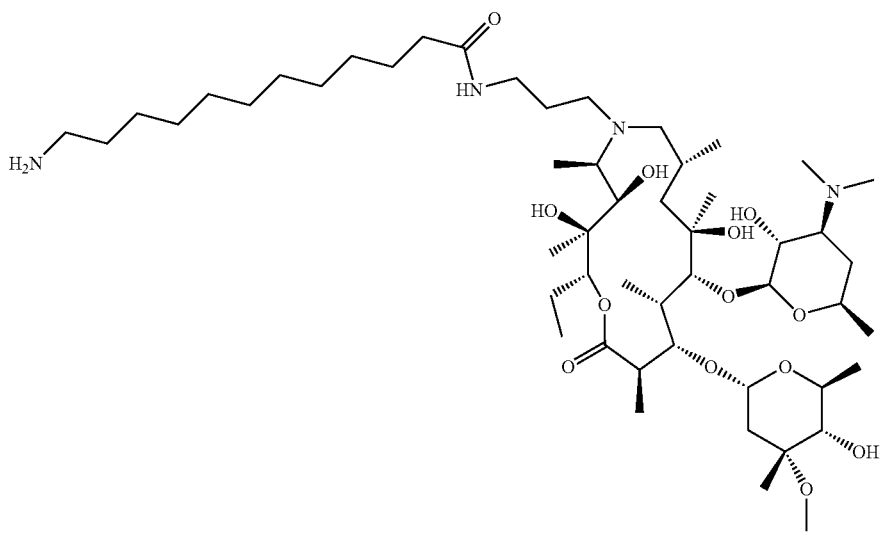 |

-continued

| EXPERIMENTAL | |
|---|---|
| Macrolide | Structure |
| M12 | 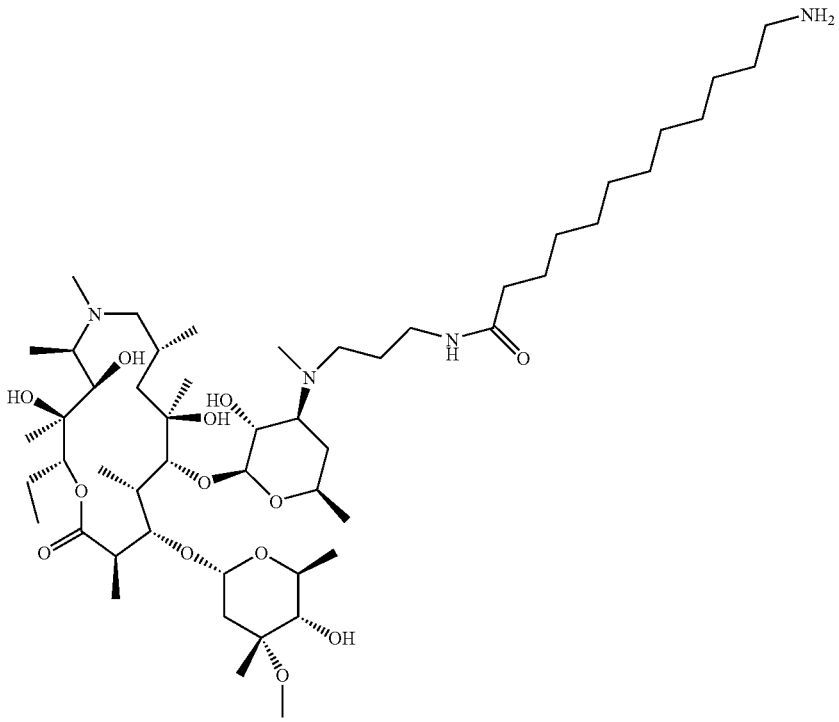 |

Azithromycin amines M1 and M2 may be prepared by procedure as described in international patent application WO 02/055531 A1. Amine M3 may be prepared by procedure as described in international patent application WO 2004/09449 A1. Amine M4 and M6 may be prepared by procedure as described in international patent application WO 2004/005310 A2.

Amines M5, M7 and M10 may be prepared by the same procedure as they were prepared by in U.S. provisional application 60/643,841, herein incorporated by reference in its entirety. More particularly, M5 can be prepared by stirring a solution of 2'-O-Acetyl-11-O-methyl-azithromycin in acrylonitrile with t-BuOH and NaH under nitrogen at 0° C. for 1 hour. The acrylonitrile is evaporated and the residue dissolved in DCM and extracted with water. The organic layer is filtered, dried, and dissolved in glacial HOAc with PtO2. The reaction mixture is hydrogenated in a Parr apparatus, the solvent and catalyst removed, and the compound extracted, dried, and dissolved in MeOH. The product is obtained after stirring the mixture at 50° C. for 18 hours and evaporating the MeOH.

To obtain M7, a solution containing 11,12-carbonate-11,12-dideoxy-2'-O-acetyl-6-O-methylerythromycin A 9-O-(1-isopropoxycyclohexyl)oxime is reacted under conditions similar to those described for M5, except for (a) the residue is dissolved in ethyl acetate instead of DCM, and (b) the product obtained is mixed with CHOOH and $Na_2S_2O_5$, and dissolved in $EtOH/H_2O$. The reaction mixture is warmed up to 80° C. and stirred. After evaporation of the solvent, dilution, pH adjustment, extraction of the organic layer, drying, and purification, compound M7 is obtained.

To obtain the macrolide M10, diethylamine is added to a solution of compound 2'-O-acetyl-4''-O-propenoyl-6-O-methyl-9a-aza-9a-homoerythromycin A (prepared according to WO 03/042228, incorporated by reference) in dry methanol. The reaction mixture is stirred overnight at 40° C. The product is mixed in acrylonitrile and refluxed over the night. Following deprotection of 2'-O-acetyl group the intermediate is dissolved in glacial acetic acid in the presence of $PtO_2$ and stirred under a hydrogen atmosphere overnight. Filtration, evaporation, and purification give the M10 product.

Compound M9 may be prepared according to procedure as described in international patent application WO 03/042228 A1.

EXAMPLE 1

Compound 1

To a suspension of biotin (70 mg; 0.29 mmol) in dry $CH_2Cl_2$ (5 mL) under argon, triethylamine (0.380 mL, 2.73 μmmol); 1-hydroxybenzotriazole (80 mg, 0.59 mmol); amine M1 (230 mg, 0.29 mmol) and 1-(3-dimethylaminopropyl)-3-ethyl-carbodiimide hydrochloride (235 mg, 1.23 mmol) were added. The reaction mixture was stirred at room temperature in a flow of argon for 24 hours and then evaporated to a smaller volume and purified on a silica gel column (eluent: $CHCl_3:CH_3OH:NH_4OH=6:1:0.1$) affording compound 1 (166 mg).

MS (m/z): 1018.40 $[MH]^+$.

EXAMPLE 2

Compound 2

The compound 2 is prepared starting from amine M1 and 2-iminobiotin according to the procedure described in Example 1.

EXAMPLE 3

Compound 3

To a solution of Sulfo-SBED (Sulfosuccinimidyl-2-[6-(biotinamido)-2-(p-azidobenzamido)hexanoamido]ethyl-1,3'-dithiopropionate (10 mg, 0.011 mmol); obtained from PIERCE, Rockford, Ill., USA) in dry DMF (500 µL) the amine M1 (9 mg, 0.011 mmol) was added and stirred in the dark at room temperature for two hours. The mixture was then concentrated under reduced pressure. The residue was purified by column chromatography (eluent: $CH_2Cl_2$:MeOH:$NH_4OH$=6/1/0.1), affording the compound 3 (12 mg). MS (m/z): 1454.60 $[MH]^+$.

EXAMPLE 4

Compound 4

The compound 4 (12.84 mg) was prepared starting from amine M5 (9.7 mg, 0.011 mmol) according to the procedure described in Example 3.

MS (m/z): 1468.34 $[MH]^+$.

EXAMPLE 5

Compound 5

The compound 5 is prepared starting from macrolide M9. The macrolide is mixed with 5-(biotinamido)pentylamine in methanol and reacted at 55° C. overnight. The mixture is then concentrated under reduced pressure. The residue is purified by column chromatography (eluent: $CH_2Cl_2$:MeOH:$NH_4OH$=6/1/0.1) affording the compound 5.

EXAMPLE 6

Compound 6

The compound 6 is prepared starting from amine M10 according to the procedure described in Example 3.

EXAMPLE 7

Compound 7

The compound 7 is prepared starting from amine M2 according to the procedure described in Example 3.

EXAMPLE 8

Compound 8

The compound 8 is prepared starting from amine M3 according to the procedure described in Example 3.

EXAMPLE 9

Compound 9

The compound 9 (9.55 mg) was prepared starting from amine M4 (9 mg, 0.011 mol) according to the procedure described in Example 3.

MS (m/z): 1455.32 $[MH]^+$.

EXAMPLE 10

Compound 10

The compound 10 (7.19 mg) was prepared starting from amine M6 (9 mg, 0.011 mmol) according to the procedure described in Example 3.

MS (m/z): 1455.37 $[MH]^+$.

EXAMPLE 11

Compound 11

Amine M11

To a suspension of 12-(FMOC-amino)dodecanoic acid (254 mg, 0.058 mmol) in dry $CH_2Cl_2$ (5 mL) under argon triethylamine (0.760 mL); 1-hydroxybenzotriazole (160 mg); M1 (460 mg, 0.058 mmol) and 1-(3-dimethylaminopropyl)-3-ethyl-carbodiimide hydrochloride (470 mg) were added. The reaction mixture was stirred at room temperature for 24 hours and then evaporated to a smaller volume and purified on a silica gel column (eluent: $CHCl_3$:$CH_3OH$:$NH_4OH$=6:1:0.1). The FMOC protected compound (137 mg) was dissolved in ethyl acetate (5 mL), piperidine (2 mL) was added and resulting reaction mixture was stirred at room temperature for 3 hours and then concentrated under reduced pressure affording the amine Ml (140 mg).

Compound 11

The compound 11 (23 mg) was prepared starting from amine M11 (100 mg) according to the procedure described in Example 1.

MS (m/z): 1215.42 $[MH]^+$.

EXAMPLE 12

Compound 12

Amine M12

The amine M12 (299 mg) was prepared starting from amine M4 according to procedure for amine Ml of Example 11.

Compound 12

The compound 12 (36 mg) was prepared starting from amine M12 (150 mg) according to the procedure described in Example 1.

MS (m/z): 1215.87 $[MH]^+$.

EXAMPLE 13

Compound 13

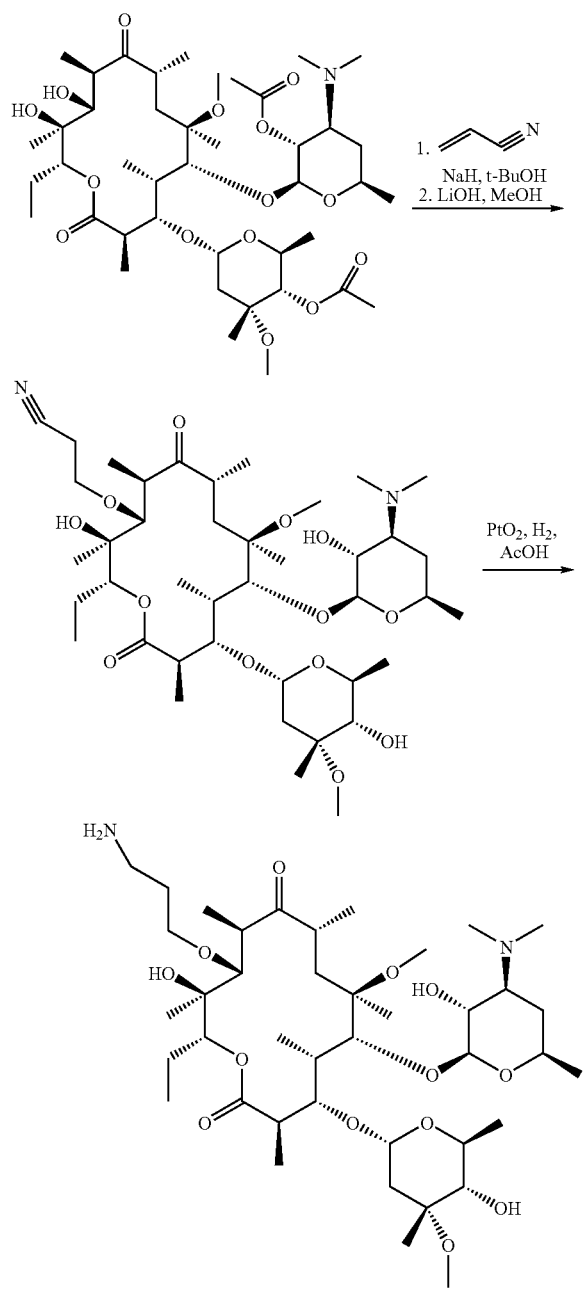

Step 1: 11-cyanoethoxy clarithromycin

2',4"-O-di-Acetyl clarithromycin (1.24 g, 1.49 mmol) was dissolved in acrylonitrile (29.5 ml) and stirred at room temperature. Tert-butanol (0.14 ml) was added, solution cooled to 0° C., then NaH (0.06 g, 2.50 mmol) was added and the reaction was stirred for 24 hours at room temperature. After the reaction was completed acrylonitrile was evaporated under reduced pressure. Water (20 ml) and dichloromethane (20 ml) were added and layers were separated. The organic layer was extracted with saturated aqueous solution NaHCO$_3$, water and brine. The organic layer was dried over anhydrous Na$_2$SO$_4$, filtered and the solvent was evaporated under reduced pressure to give di-acetyl protected cyano clarithromycin (1.85 g) which after deprotection in methanol with LiOH gave 11-cyanoethoxy clarithromycin (1.04 g).

MS: m/z=801.4 [M+H]$^+$

Step 2: Amine M8

The compound obtained in step 1 (0.26 g, 0.32 mmol) was dissolved in glacial acetic acid (15 ml) at room temperature and platinum (IV)-oxide (0.1 g, 0.44 mmol) was added. The reaction mixture was hydrogenated under a pressure of 4.5 bar for 5 hours, catalyst was removed by filtration and filtrate concentrated in vacuum to give crude product. Then, dichloromethane and water were added to the crude product. Gradient extraction at 7.6 and 9.5 was performed, after evaporation of organic layer obtained at pH 9.5, the amine M8 (0.62 g) was obtained.

MS: m/z=805.7 [M+H]$^+$

Compound 13

The compound 13 (8.16 mg) was prepared starting from amine M8 (9 mg, 0.011 mmol) according to the procedure described in Example 3.

MS (m/z): 1467.80 [MH]$^+$.

EXAMPLE 14

Compound 14

The compound 14 (5.65 mg) was prepared starting from amine M7 (9 mg/0.011 mmol) according to the procedure described in Example 3.

MS (m/z): 1467.60 [MH]$^+$.

EXAMPLE 15

The compound from Example 9 (1 mM) was dissolved in dimethyl sulfoxide (20 μL) (Kemika, Croatia) and was incubated with human serum (obtained from the venous blood of a healthy volunteer) for 60 minutes at room temperature in the dark. Afterwards, the mixture was irradiated by ultraviolet light (365 nm) for 15 minutes in Spectroline CX-20 Ultraviolet Analysis Cabinet (Spectronics, USA) and then incubated overnight with Streptavidin Sepharose matrix (Amersham Biosciences, Sweden) at 4° C. The matrix was washed with phosphate buffer, pH 7.5 (20 mM), containing NaCl (150 mM) and briefly centrifuged in order to remove the unbound protein fraction. The procedure was repeated three times. Compound 9 covalently bound to proteins was eluted from matrix with guanidine-hydrochloride, pH 1.5 (8 M). Afterwards, proteins were precipitated using ProteoExtract Protein Precipitation Kit (Calbiochem, USA) and separated by SDS electrophoresis on polyacrylamide gel. α$_1$-Acid glycoprotein was detected by Western blot using monoclonal antibodies (Sigma, USA) (See FIG. 1).

This confirms that α$_1$-acid glycoprotein from human serum is one of the proteins that binds to compound 9. Similarly, this approach can be used to identify other proteins that interact with compounds of the present invention.

What is claimed is:
1. A compound according to Formula I:

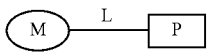

wherein
M represents a macrolide subunit of the substructure II:

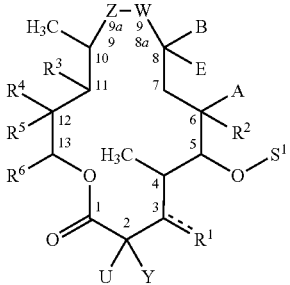

wherein
(i) Z and W independently are

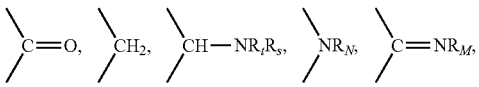

or a bond, wherein
$R_t$ and $R_s$ independently are H or alkyl;
$R_M$ is OH, $OR^p$, alkoxy or substituted alkoxy;
$R_N$ is H, $R^p$, alkyl, alkenyl, alkynyl, alkoxy, alkoxyalkyl, or —C(=X)—$NR_tR_s$; and
X is O or S;
provided that Z and W cannot both simultaneously be

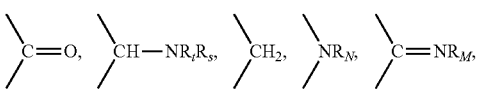

or a bond,
(ii) U and Y are independently H, halogen, alkyl, or hydroxyalkyl;
(iii) $R^1$ is hydroxy, $OR^p$, —O—$S^2$, or =O;
(iv) $S^1$ is H or a sugar moiety at position C/5 of the formula:

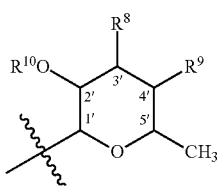

wherein
$R^8$ and $R^9$ are both hydrogen or together form a bond, or $R^9$ is hydrogen and $R^8$ is —N(CH$_3$)$R^y$, wherein $R^y$ is $R^p$, $R^z$ or —C(O)$R^z$, wherein $R^z$ is hydrogen, cycloalkyl, alkyl, alkenyl, alkynyl or heteroaryl, or an alkyl substituted with $C_2$-$C_7$ alkyl, $C_2$-$C_7$ alkenyl, $C_2$-$C_7$ alkynyl, aryl or heteroaryl;
$R^{10}$ is hydrogen or $R^p$;
(v) $S^2$ is a sugar moiety of the formula

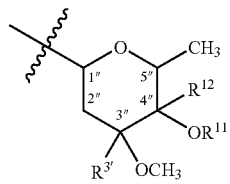

wherein $R^{3'}$ is H or methyl and $R^{11}$ is hydrogen, $R^p$, —C(O)(CH$_2$)$_q$NR$^4$R$^6$, or O—$R^{11}$ is a group that with $R^{12}$ and with C/4" carbon atom forms a >C=O or epoxy group; $R^{12}$ is hydrogen or a group that with O—$R^{11}$ and with C/4" carbon atom forms a >C=O or epoxy group,
wherein q is an integer from 1 to 6;
(vi) $R^2$ is H, hydroxy, $OR^p$ group, alkoxy or substituted alkoxy;
(vii) A is H or methyl;
(viii) B is methyl or epoxy;
(ix) E is H or halogen;
(x) $R^3$ is hydroxy, $OR^p$ group or alkoxy, substituted alkoxy or $R^3$ is a group that can combine with $R^5$ to form a "bridge" or if W or Z is

$R^3$ is a group that can combine with W or Z to form a "bridge";
(xi) $R^4$ is $C_1$-$C_4$ alkyl;
(xii) $R^5$ is H, hydroxy, $OR^p$ group, $C_1$-$C_4$ alkoxy, substituted alkoxy or a group that may combine with $R^3$ to form a bridge;
(xiii) $R^6$ is H or $C_1$-$C_4$ alkyl;
(xiv) RP is a protective group selected from alkyl, alkanoyl, alkoxycarbonyl, arylmethoxycarbonyl, aroyl, arylalkyl, alkylsilyl and alkylsilylalkoxyalkyl;
wherein the subunit M has a linkage site through which it is linked to the subunit P via the linking group L, the linkage of L to the macrolide moiety is either through:
a. the ring nitrogen atom at position 9a;
b. the hydroxy group at position 11 or position 6;
c. the 2' hydroxyl or the 3' amino group of the desozamine sugar moiety;
d. the 4" dhyroxy group of the cladinose sugar or;
e. if the M moiety is aglycone or missing one of the desozamine and cladinose sugar groups, through the OH group created at position 5 or 3 or the macrolide ring;
L is a linking molecule represented by the Formula IIIA or IIIB:

$X^1$—(CH$_2$)$_m$—$X^2$ or         IIIA $X^1$—(CH$_2$)$_m$-Q-(CH$_2$)$_n$—$X^2$         IIIB wherein
$X^1$ is selected from: —CH$_2$, —CH$_2$—NH—, —C(O)—, —OC(O)—, =N—O—, —OC(O)NH— or —C(O)NH—;

$X^2$ is selected from: —NH—, —CH$_2$—; —NHC(O)—, —C(=O)—, —O— or —OC(O)—;

Q is —NH—, —CH$_2$— or —S—S—;

wherein each —CH$_2$— or —NH—group is optionally substituted by C$_1$-C$_7$-alkyl, C$_2$-C$_7$alkenyl, C$_2$-C$_7$alkynyl, C(O)R$^x$, C(O)OR$^x$, C(O)NHR$^x$ wherein R$^x$ may be C$_1$-C$_7$-alkyl, aryl or heteroaryl;

the symbols m and n are independently a whole number from 0 to 8 with the proviso that if Q=NH; n cannot be zero;

P represents a photo-affinity group containing a biotin or iminobiotin subunit that is represented by the substructure IV:

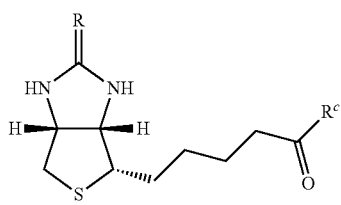

IV wherein
R$^c$ is the covalent link chain L at X$^2$;
R is O or NH:

or P represents a subunit containing biotin and a photo-affinity group that is represented by the substructure V:

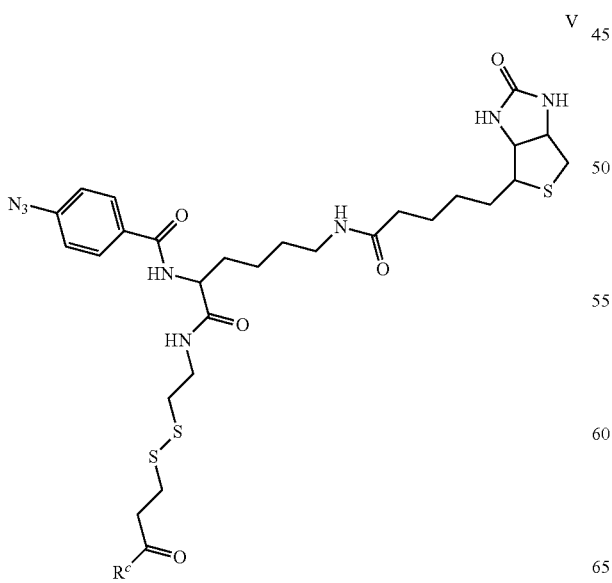

V wherein
R$^c$ is a covalent link with chain L at X$^2$;

wherein:

alkyl represents a linear or branched saturated monovalent hydrocarbon radical of one to ten carbon atoms, unsubstituted or substituted with one up to five substituents selected from halogen, hydroxy, alkoxy, acyl, acylamino cyano, amino, N—(C$_1$-C$_4$)alkylamino, N,N-di(C$_1$-C$_4$-alkyl)amino, aryl, heteroaryl, thiocarbonylamino, acyloxy, amino, amidino, alkyl amidino, thioamidino, aminoacyl, aminocarbonylamino, aminothiocarbonylamino, aminocarbonyloxy, aryloxy, aryloxyaryl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, cycloalkoxy, heteroaryloxy, heterocyclyloxy and oxycarbonylamino, wherein term alkyl has the above defined meaning in all other substituent groups;

alkenyl represents a linear or branched monovalent hydrocarbon radical of two to ten carbon atoms which has at least one double carbon-carbon bond, unsubstituted or substituted with the same groups as defined above for alkyl group;

alkynyl represents a linear or branched monovalent hydrocarbon radical, having a straight-chain or a branched-chain of two to ten, and containing from one to three triple carbon-carbon bonds, unsubstituted or substituted with the same groups as defined above for alkyl group;

cycloalkyl represents a cyclic group having three to eight carbon atoms having a single ring optionally fused to an aryl or heteroaryl group, or optionally fused to a saturated ring, cycloalkyl is unsubstituted or substituted with one or more substituents selected from halogen, hydroxy, C$_1$-C$_7$ alkyl, C$_1$-C$_7$ alkoxy, C$_1$-C$_7$ aryloxy, C$_1$-C$_7$ alkylthio, arylthio, alkylsulfonyl, cyano, primary amino, nonprimary amino, haloalkyl and alkylamino;

aryl represents an unsaturated aromatic carbocyclic group having 6-14 carbon atoms having a single ring or multiple fused rings, optionally further fused to an aliphatic or aryl group, aryl is unsubstituted or substituted with one or more substituents selected from halogen, hydroxy, C$_1$-C$_7$ alkyl, C$_1$-C$_7$ alkoxy, C$_1$-C$_7$ aryloxy, C$_1$-C$_7$ alkylthio, arylthio, alkylsulfonyl, cyano, primary amino, nonprimary amino, haloalkyl and alkylamino;

heteroaryl represents a monocyclic or a bicyclic aromatic hydrocarbon ring having from 2 to 10 carbon atoms and from 1 to 4 heteroatoms selected from O, S and N, optionally fused to another heteroaryl, aryl or aliphatic cyclic group, heteroaryl is unsubstituted or substituted with the same substituents as defined above for aryl group; and heterocyclic represents a saturated or unsaturated group having a single or multiple rings and from 1 to 10 carbon atoms and from 1-4 heteroatoms selected from N, S and O, wherein in a fused ring system the other ring or rings can be aryl or heteroaryl, heterocyclic group is unsubstituted or substituted as specified above for alkyl group.

2. A compound according to claim 1 wherein the photo-affinity group is arylazide.

3. A compound according to claim 1 wherein P is represented by the substructure V:

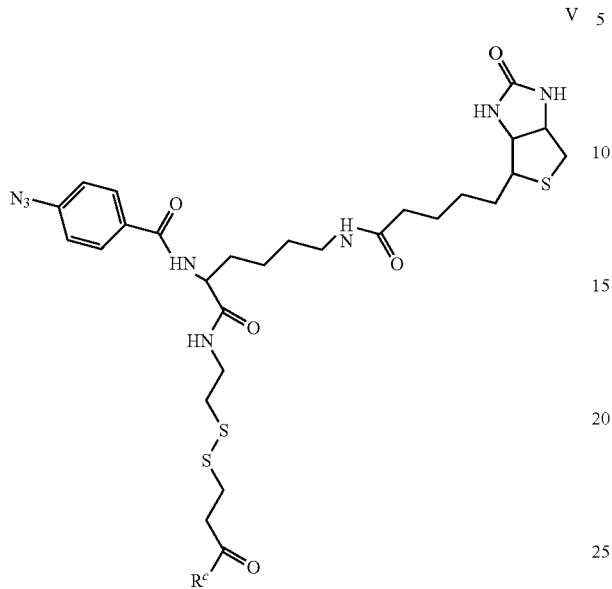

wherein
$R^c$ is the covalent link with $X^2$ of chain L.

4. A compound according to claim 1, having the following features (i) through (x):
  (i) Z and W independently are

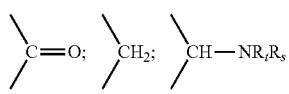

wherein $R_t$ and $R_s$ independently are H or methyl;

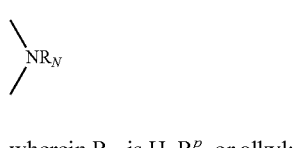

wherein $R_N$ is H, $R^p$, or alkyl;

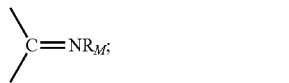

or a bond;
  (ii) U and Y are independently H, methyl, or hydroxymethyl;
  (iii) $R^9$ is hydrogen and $R^8$ is —N(CH$_3$)R$^y$, wherein R$^y$ is $R^p$, $R^z$ or —C(O)R$^z$, wherein $R^z$ is hydrogen or cyclohexyl, $C_1$-$C_7$ alkyl, $C_2$-$C_7$-alkenyl, $C_2$-$C_7$-alkynyl, aryl or heteroaryl or alkyl substituted with $C_2$-$C_7$ alkyl, $C_2$-$C_7$ alkenyl, $C_2$-$C_7$ alkynyl, aryl or heteroaryl;
  (iv) $R^2$ is $C_1$-$C_4$ alkoxy;
  (v) E is H or fluorine;
  (vi) $R^3$ is hydroxy, OR$^p$ group, $C_1$-$C_4$ alkoxy;
  (vii) $R^4$ is a methyl;
  (viii) $R^6$ is methyl or ethyl;
  (ix) at least one $R^p$ is present and $R^p$ represents a protective group selected from methyl, acetyl, methoxycarbonyl or tert-butoxycarbonyl, benzyloxycarbonyl, benzoyl, benzyl, trimethylsilyl, or trimethylsilylethoxymethyl;
  (x) $R^1$ is hydroxyl and $S^1$ is a sugar moiety of the formula

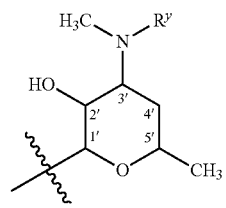

wherein R$^y$ is as defined in claim 1.

5. A method for identifying a substance selected from the group of proteins, peptides or polypeptides having binding affinity for macrolides comprising:
  contacting a sample potentially containing said substance with a compound according to claim 1 under conditions permitting said compound to bind to said substance;
  activating said photo affinity group; and
  determining whether said compound binds said substance by assessing the strength of said signal compared to background or to a pre-established standard.

6. A compound according to claim 1, having the following features (i) through (x):
  (i) Z and W independently are

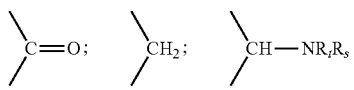

wherein $R_t$ and $R_s$ independently are H or methyl;

wherein $R_N$ is H, $R^p$, or alkyl;

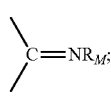

or a bond;
  (ii) U and Y are independently H, methyl, or hydroxymethyl;
  (iii) $R^9$ is hydrogen and $R^8$ is —N(CH$_3$)R$^y$, wherein R$^y$ is $R^p$, $R^z$ or —C(O)R$^z$, wherein $R^z$ is hydrogen or cyclohexyl, $C_1$-$C_7$ alkyl, $C_2$-$C_7$-alkenyl, $C_2$-$C_7$-alkynyl, aryl or heteroaryl or alkyl substituted with $C_2$-$C_7$ alkyl, $C_2$-$C_7$ alkenyl, $C_2$-$C_7$ alkynyl, aryl or heteroaryl;
  (iv) $R^2$ is $C_1$-$C_4$ alkoxy;
  (v) E is H or fluorine;
  (vi) $R^3$ is hydroxy, OR$^p$ group, $C_1$-$C_4$ alkoxy;
  (vii) $R^4$ is a methyl;
  (viii) $R^6$ is methyl or ethyl;
  (ix) at least one $R^p$ is present and $R^p$ represents a protective group selected from methyl, acetyl, methoxycarbonyl or tert-butoxycarbonyl, benzyloxycarbonyl, benzoyl, benzyl, trimethylsilyl, or trimethylsilylethoxymethyl;
  (x) $S^1$ is hydrogen and $R^1$ is hydroxyl.

* * * * *